(12) United States Patent
Lecomte et al.

(10) Patent No.: US 11,179,329 B2
(45) Date of Patent: *Nov. 23, 2021

(54) THERAPEUTICAL USE OF H3-LIGANDS

(71) Applicant: BIOPROJET Pharma, Paris (FR)

(72) Inventors: Jeanne-Marie Lecomte, Paris (FR); Jean-Charles Schwartz, Paris (FR); Olivier Labeeuw, Fougeres (FR); Marc Capet, Melesse (FR)

(73) Assignee: BIOPROJET PHARMA, Paris (FR)

( * ) Notice: Subject to any disclaimer, the term of this patent is extended or adjusted under 35 U.S.C. 154(b) by 0 days.

This patent is subject to a terminal disclaimer.

(21) Appl. No.: 16/496,126

(22) PCT Filed: Mar. 21, 2018

(86) PCT No.: PCT/EP2018/057215
§ 371 (c)(1),
(2) Date: Sep. 20, 2019

(87) PCT Pub. No.: WO2018/172432
PCT Pub. Date: Sep. 27, 2018

(65) Prior Publication Data
US 2020/0093738 A1    Mar. 26, 2020

(30) Foreign Application Priority Data
Mar. 21, 2017 (EP) .................................. 17305309

(51) Int. Cl.
| | | |
|---|---|---|
| *A61K 31/4545* | (2006.01) | |
| *A61K 9/00* | (2006.01) | |
| *A61P 25/20* | (2006.01) | |
| *C07D 401/12* | (2006.01) | |
| *A61P 25/28* | (2006.01) | |
| *A61P 25/16* | (2006.01) | |

(52) U.S. Cl.
CPC ........ *A61K 9/0053* (2013.01); *A61K 31/4545* (2013.01); *A61P 25/16* (2018.01); *A61P 25/20* (2018.01); *A61P 25/28* (2018.01); *C07D 401/12* (2013.01)

(58) Field of Classification Search
CPC ... A61K 9/0053; A61K 31/4545; A61P 25/32; A61P 25/00; A61P 25/24; A61P 25/16; A61P 25/08; A61P 3/00; A61P 3/10; A61P 43/00; A61P 25/28; C07D 401/12
USPC .......................................... 546/193; 514/316
See application file for complete search history.

(56) References Cited

U.S. PATENT DOCUMENTS

2020/0024256 A1* 1/2020 Capet ..................... A61P 25/18

FOREIGN PATENT DOCUMENTS

WO    WO 2006/117609 A2    11/2006

OTHER PUBLICATIONS

Khankari et al, Pharmacutical hydrates, Thermochimica Acta 248 (1995) 61-79., (Year: 1995).*
Extended European Search Report issued in corresponding European Patent Application No. 17305309.1 dated Aug. 4, 2017.
International Search Report issued in corresponding International Patent Application No. PCT/EP2018/057215 dated May 15, 2018.

* cited by examiner

*Primary Examiner* — Taylor V Oh
(74) *Attorney, Agent, or Firm* — Troutman Pepper Hamilton Sanders LLP

(57) ABSTRACT

The present invention concerns new therapeutical uses, including low dosage administration of the highly potent H3-ligand: (3S)-4-{4-[3-(3-methylpiperidin-1-yl)propoxy]phenyl}pyridine 1-oxide.

18 Claims, No Drawings

THERAPEUTICAL USE OF H3-LIGANDS

CROSS REFERENCE TO RELATED APPLICATIONS

This is a U.S. National Phase Application under 35 U.S.C. § 371 of International Patent Application No. PCT/EP2018/057215, filed Mar. 21, 2018, which claims priority of European Patent Application No. 17305309.1, filed Mar. 21, 2017. The entire contents of which are hereby incorporated by reference.

FIELD OF THE INVENTION

The present invention concerns new therapeutical use, including low dosage administration of a highly potent histamine H3-receptor ligand.

WO 2006/117609 discloses non-imidazole histamine H3 ligands of formula:

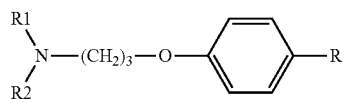

and their use for treating and/or preventing CNS disorders such as Alzheimer's disease; attention; wakefulness and memorization disorders; cognitive deficits in psychiatric pathologies; disorders in aged persons; depressive or asthenic states; Parkinson's disease; obstructive sleep apnea; dementia with Lewy bodies; vascular dementia; vertigo; motion sickness; alcohol and other substance abuse; chronic pain; obesity; diabetes and the metabolic syndrome; sleep disorders; stress; psychotropic disorders; convulsion; depression; narcolepsy; disorders of the hypothalamohypophyseal secretion, the cerebral circulation and/or immune system; and/or for facilitating night works or adaptation to time shift in healthy humans.

BACKGROUND

WO 2006/117609 discloses that said ligands are generally suitable for administration to humans of unit doses generally comprised between 0.1 mg to 1000 mg per day, preferably from 1 to 500 mg administered one to four times a day, and even more preferably from 10 mg to 300 mg, two times a day.

Similarly, pitolisant, another non-imidazole H3 antagonist authorized for treating narcolepsy is marketed in unit dosage forms (coated tablets) of 4.5 mg and 18 mg. The optimal authorized therapeutical dose can be up to 36 mg a day.

Generally speaking, it is desired to identify drug candidates that are as potent as possible. Higher potency is generally associated with high selectivity towards the target, lower risks to bind to off-targets and, therefore higher clinical safety.

It is thus desirable to identify drug candidates that are as high potent as possible and that have effective doses as low as possible.

Among the H3 ligands disclosed in WO 2006/117609 and despite the disclosed doses of H3-ligands, the inventors have now found that (3S)-4-{4-[3-(3-methylpiperidin-1-yl)propoxy]phenyl}pyridine 1-oxide of formula:

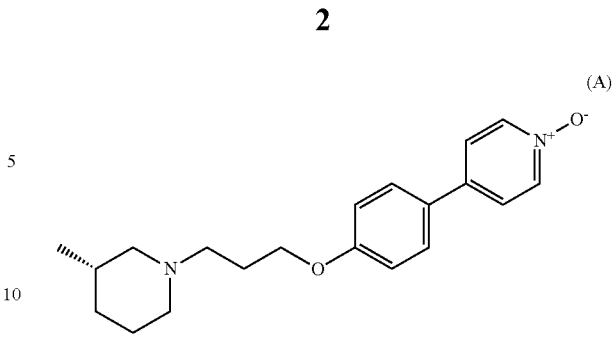

herein referred as "compound (A)", unexpectedly exhibits an outstanding profile which thus allows substantially low effective doses.

SUMMARY

According to a first object, the present invention thus concerns (3S)-4-{4-[3-(3-methylpiperidin-1-yl)propoxy]phenyl}pyridine 1-oxide of formula (A):

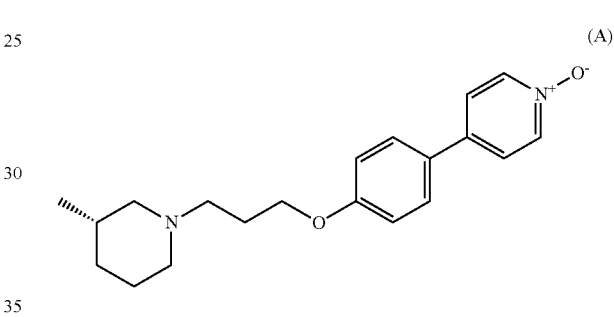

or its pharmaceutically acceptable salts and/or the solvates of said compound (A) or of its salts, for use for treating and/or preventing in a human patient disorders selected from Alzheimer's disease; attention; wakefulness and memorization disorders; cognitive deficits in psychiatric pathologies; cognitive, mood and vigilance disorders in particular in aged persons; depressive or asthenic states; Parkinson's disease; obstructive sleep apnea; dementia with Lewy bodies; vascular dementia; vertigo; motion sickness; obesity; diabetes and the metabolic syndrome; sleep disorders; stress; psychotropic disorders; epilepsy; depression; narcolepsy with or without cataplexy; substance abuse, notably alcohol abuse disorders, prevention of substance abuse withdrawal syndromes; cognitive disorders in autism; chronic pain and chronic fatigue; post-stroke fatigue, mood, vigilance and cognitive disorders; attention and vigilance disorders of ADHD (attention-deficit hyperactivity disorder) in children or adults or following cerebrovascular accidents; disorders of the hypothalamohypophyseal secretion, the cerebral circulation and/or immune system; excessive daytime sleepiness, such as excessive daytime sleepiness and fatigue associated with Parkinson's disease, obstructive sleep apnea or dementia; and/or for facilitating night works or adaptation to time shift in healthy humans, where said use comprises the administration of (A) in a human at a dose comprised between 10 and 90 µg a day (relative to compound (A) in the form of the base).

It is also disclosed herein a method of prevention and/or treatment of the above disorders comprising the administration of compound (A) at a dose comprised between 10 and 90 µg a day (relative to compound (A) in the form of the base), with a pharmaceutically acceptable carrier or excipient, to a patient in the need thereof.

According to an embodiment, the use is for treating and/or preventing sleep disorders such as insomnia, disorders of sleep initiation and maintenance, sleep fragmentation, parasomnias, REM sleep disorders, sleep disordered breathing, circadian dysrhythmia, narcolepsy with or without cataplexy, excessive daytime sleepiness (including "sleep attacks"), such as fatigue or excessive daytime sleepiness associated with Parkinson's disease, obstructive sleep apnea or dementia. Another use is for the treatment and/or prevention of substance abuse disorders, notably alcohol abuse. Another use is for the treatment and/or prevention of mood, cognitive and vigilance disorders associated with stroke. Another use is for treating and/or preventing cognitive and attention disorders in ADHD or following cerebrovascular accidents.

According to an embodiment, the compound (A) is in the form of its base, as depicted in formula (A). Alternatively, compound (A) may be in the form of pharmaceutically acceptable salts such as hydrochloride, oxalate, dihydrochloride, hydrobromide, dihydrobromide, naphthalene-1,5-disulfonate, sulfate, ethane-1,2-disulfonate, cyclamate, toluenesulfonate, paratoluenesulfonate, thiocyanate, nitrate, methanesulfonate, dodecylsulfate, naphthalene-2-sulfonate, benzenesulfonate, dichloroacetate, glycerophosphate, 2-hydroxyethanesulfonate, aspartate, maleate, phosphate, ethanesulfonate, camphor-10-sulfonate, glutamate, alginate, pamoate, 2-oxo-glutarate, 1-hydroxy-2-naphthoate, malonate, gentisate, salicylate, tartrate, fumarate, galactarate, citrate, glucuronate, lactobionate, 4-aminosalicylate, glycolate, sesquiglycolate, glucoheptonate, pyroglutamate, mandelate, malate, hippurate, formate, gluconate, lactate, oleate, ascorbate, benzoate, succinate, 4-acetamidobenzoate, glutarate, cinnamate, adipate, sebacate, camphorate, acetate, caproate, nicotinate, isobutyrate, proionate, carate, laurate, palmitate, stearate, undecen-10-oate, caprylate, orotate, carbonate, 5-sulfocalicylate, 1-hydroxy-2-naphthoate, 3-hydroxy-2-naphthoate; and/or solvates such as hydrates, ethanolate, hemiethanolate.

Accordingly, the expression "compound (A)" as used herein also refers to the pharmaceutically acceptable salts thereof and/or the solvates of said compound of formula (A) or of the salts thereof, unless specified otherwise. The dihydrochloride salt is particularly mentioned.

The expression "compound (A) in the form of a base" corresponds to compound (A) as depicted above.

According to an embodiment, Compound (A) may be in the form of the following pharmaceutically acceptable salts:
- (3S)-4-{4-[3-(3-methylpiperidin-1-yl)propoxy]phenyl}pyridine 1-oxide dihydrochloride tetrahydrate
- (3S)-4-{4-[3-(3-methylpiperidin-1-yl)propoxy]phenyl}pyridine 1-oxide oxalate;
- (3S)-4-{4-[3-(3-methylpiperidin-1-yl)propoxy]phenyl}pyridine 1-oxide L-tartrate and its trihydrate;
- (3S)-4-{4-[3-(3-methylpiperidin-1-yl)propoxy]phenyl}pyridine 1-oxide pamoate;
- (3S)-4-{4-[3-(3-methylpiperidin-1-yl)propoxy]phenyl}pyridine 1-oxide fumarate;
- (3S)-4-{4-[3-(3-methylpiperidin-1-yl)propoxy]phenyl}pyridine 1-oxide para-toluenesulfonate and its sestertihydrate (2.5)
- (3S)-4-{4-[3-(3-methylpiperidin-1-yl)propoxy]phenyl}pyridine 1-oxide 1,5-naphtalenedisulfonate and its hemiethanolate monohydrate;
- (3S)-4-{4-[3-(3-methylpiperidin-1-yl)propoxy]phenyl}pyridine 1-oxide phosphate;
- (3S)-4-{4-[3-(3-methylpiperidin-1-yl)propoxy]phenyl}pyridine 1-oxide bromhydrate;
- (3S)-4-{4-[3-(3-methylpiperidin-1-yl)propoxy]phenyl}pyridine 1-oxide 1,2-ethanedisulfonate;
- (3S)-4-{4-[3-(3-methylpiperidin-1-yl)propoxy]phenyl}pyridine 1-oxide sulfate;
- (3S)-4-{4-[3-(3-methylpiperidin-1-yl)propoxy]phenyl}pyridine 1-oxide dibromhydrate;
- (3S)-4-{4-[3-(3-methylpiperidin-1-yl)propoxy]phenyl}pyridine 1-oxide orotate and its dihydrate;
- (3S)-4-{4-[3-(3-methylpiperidin-1-yl)propoxy]phenyl}pyridine 1-oxide 5-sulfosalicylate;
- (3S)-4-{4-[3-(3-methylpiperidin-1-yl)propoxy]phenyl}pyridine 1-oxide 1-hydroxy-2-naphtoate and its monohydrate;
- (3S)-4-{4-[3-(3-methylpiperidin-1-yl)propoxy]phenyl}pyridine 1-oxide 3-hydroxy-2-naphtoate;
- (3S)-4-{4-[3-(3-methylpiperidin-1-yl)propoxy]phenyl}pyridine 1-oxide (sesqui)glycolate and its monohydrate.

According to an embodiment, it is in the form of the tetrahydrate form of the dihydrochloride of compound (A).

The tetrahydrate of compound (A) is stable for relative humidity ranging from at least 30% to 70% which is an improved property as compared to the hygroscopic nature of the previously described dihydrochloride. The tetrahydrate of compound (A) is also stable for temperatures ranging from 20° C. to 40° C.

The tetrahydrate of compound (A) exhibits one or more of the following features: According to an embodiment, the tetrahydrate form of compound (A) exhibits a melting peak around 191° C. when measured by capillary tube method.

According to another embodiment, analysis by differential scanning calorimetry shows two endothermic events with onset around 53° C. and 83° C. which correspond to the loss of four water molecules; a last event is observed with an onset around 191° C.

According to another embodiment, the water content of the tetrahydrate of compound (A) is comprised between 14 and 16%, generally about 15.3±0.7% in weight.

According to an embodiment, the tetrahydrate form of compound (A) exhibits one or more of the powder X-ray diffractogram lines described below:

| Angle (2-Theta °) | d value (Angstrom) | Intensity (Count) | Relative Intensity (%) |
|---|---|---|---|
| 5.1 | 17.5 | 476 | 20.9 |
| 9.7 | 9.1 | 998 | 43.8 |
| 10.2 | 8.7 | 438 | 19.2 |
| 11.1 | 8.0 | 312 | 13.7 |
| 12.5 | 7.1 | 2276 | 100 |
| 13.1 | 6.8 | 517 | 22.7 |
| 14.6 | 6.1 | 700 | 30.8 |
| 15.2 | 5.8 | 624 | 27.4 |
| 15.8 | 5.6 | 375 | 16.5 |
| 16.5 | 5.4 | 1051 | 46.2 |
| 17.4 | 5.1 | 275 | 12.1 |
| 18.2 | 4.9 | 553 | 24.3 |
| 19.0 | 4.7 | 698 | 30.7 |
| 19.5 | 4.6 | 969 | 42.6 |
| 20.5 | 4.3 | 555 | 24.4 |
| 21.0 | 4.2 | 374 | 16.4 |
| 22.0 | 4.1 | 1000 | 43.9 |
| 22.5 | 3.9 | 446 | 19.6 |
| 23.7 | 3.8 | 467 | 20.5 |
| 24.3 | 3.7 | 588 | 25.8 |
| 24.8 | 3.6 | 1386 | 60.9 |
| 25.2 | 3.5 | 408 | 17.9 |
| 26.2 | 3.4 | 1352 | 59.4 |

-continued

| Angle (2-Theta °) | d value (Angstrom) | Intensity (Count) | Relative Intensity (%) |
|---|---|---|---|
| 26.7 | 3.3 | 370 | 16.3 |
| 27.2 | 3.3 | 292 | 12.8 |
| 27.5 | 3.2 | 336 | 14.8 |
| 28.4 | 3.1 | 1058 | 46.5 |
| 29.5 | 3.0 | 527 | 23.2 |

More particularly, the following peaks:

| 2-theta (°) | d (Ångstroms) |
|---|---|
| 9.7 | 9.1 |
| 12.5 | 7.1 |
| 14.6 | 6.1 |
| 15.2 | 5.8 |
| 16.5 | 5.4 |
| 19.0 | 4.7 |
| 19.5 | 4.6 |
| 22.0 | 4.1 |
| 24.3 | 3.7 |
| 24.8 | 3.6 |
| 26.2 | 3.4 |
| 28.4 | 3.1 |

The tetrahydrate form of the dihydrochloride salt of compound (A) has been shown to be very stable.

The tetrahydrate of the dihydrochloride of compound (A) can be prepared by usual methods such as in solubilisation from a solvent by concentration, addition of an anti-solvent, and/or lowering the temperatures.

According to an embodiment, the tetrahydrate of the dihydrochloride salt of compound (A) may be prepared by a process comprising the steps of:
  dissolving the dihydrochloride of (A) into water;
  concentrating until the solid separates; and
  drying the solid up to a final water content of 15.3±0.7% in weight.

Alternatively, the tetrahydrate of the dihydrochloride of (A) can be prepared as follows:
  adding aqueous hydrochloric acid to the base (A);
  adding acetone;
  seeding until the solid separates;
  filtering; and
  drying the solid up to a final water content of 15.3±0.7% in weight.

According to an embodiment, the daily dose of compound (A) for administration to a human is comprised between 20 and 50 µg a day, preferably 30 to 45 µg of the base a day (relative to the compound (A) in the form of the base).

According to another embodiment, the method of the invention may comprise the administration of said doses of the compound (A), at a frequency comprised between once every three days, once every other day (qod), once-a-day (qd). Preferably, the administration may take place, once-a-day.

It is to be understood that the dose of the invention is the cumulative dose of each administration dose given within a day.

The identification of those subjects who are in need of treatment of herein-described diseases and conditions is well within the ability and knowledge of one skilled in the art. A clinician skilled in the art can readily identify, by the use of clinical tests, physical examination, genetic tests and medical/family history, those subjects who are in need of such treatment.

Actual dosage levels of the compound of formula (A) of the invention may be varied so as to obtain an amount of active ingredient that is effective to obtain a desired therapeutic response for a particular composition and method of administration. The selected dosage level therefore depends upon the desired therapeutic effect, on the route of administration, on the desired duration of treatment and other factors, e.g. the condition of the patient.

A therapeutically effective amount can be readily determined by the attending diagnostician, as one skilled in the art, by the use of conventional techniques and by observing results obtained under analogous circumstances. In determining the therapeutically effective amount, a number of factors are considered by the attending diagnostician, including, but not limited to: the species of subject; its size, age, and general health; the specific disease involved; the degree of involvement or the severity of the disease; the response of the individual subject; the particular compound administered; the mode of administration; the bioavailability characteristic of the preparation administered; the dose regimen selected; the use of concomitant medication; and other relevant circumstances.

The amount of compound (A) which is required to achieve the desired biological effect will vary depending upon a number of factors, including the dosage of the drug to be administered, the type of disease, the disease state of the patient and the route of administration.

In general terms, the preferred dosage of a drug to be administered is likely to depend on such variables as the type and extent of progression of the disease or disorder, the overall health status of the particular patient, the relative biological efficacy of the compound selected, and formulation of the compound excipient, and its route of administration. The daily dose of the compound (A) is generally lower than 90 µg (relative to the base) a day per patient.

According to a further embodiment, the method of the invention also comprises the administration of one or more further active ingredient, selected from anti-Parkinson drugs such as levodopa, ropinorole, lisuride, bromocriptine, pramixepole or selected from anti-narcoleptic or purported anti-narcoleptic drugs from another class including modafinil.

Compound (A) can be formulated into pharmaceutical compositions by admixture with one or more pharmaceutically acceptable excipients.

The compositions may conveniently be administered in unit dosage form and may be prepared by any of the methods well known in the pharmaceutical art, for example, as described in *Remington: The Science and Practice of Pharmacy*, 20$^{th}$ ed.; Gennaro, A. R., Ed.; Lippincott Williams & Wilkins: Philadelphia, Pa., 2000.

Compound (A) may be administered by various administration routes such as oral; parenteral including sub-cutaneous, intramuscular, intra-venous; sublingual, topical; local; intratracheal; intranasal; transdermal or rectal, the active ingredient being combined with a pharmaceutically acceptable excipient or vehicle in a pharmaceutical composition.

According to another object, the present invention thus also concerns the pharmaceutical composition comprising compound (A) and a pharmaceutically acceptable excipient or vehicle for use in treating and/or preventing the above disorders, where compound (A) is administered at a dose comprised between 10 and 70 µg a day (relative to compound (A) in the form of the base).

For the topical application, the compositions of the invention may be used as creams, gels, ointments or lotions.

In particular, the formulations suitable for parenteral administration are sterile and include emulsions, suspensions, aqueous and non-aqueous injection solutions, which may contain suspending agents and thickening agents and anti-oxidants, buffers, bacteriostats and solutes which render the formulation isotonic, and have a suitably adjusted pH, with the blood of the intended recipient.

According to the invention, oral administration of the compound or composition in an appropriate formulation is advantageously used. Formulations which are suitable to be administered orally to a patient include discrete units such as capsules, such as soft or hard gelatine, tablets, each containing a predetermined amount of the compound of formula (A). They also include powder; granules; solutions or suspensions in an aqueous liquid or a non-aqueous liquid, or oil-in-water liquid emulsion or water-in-oil liquid emulsion.

"Pharmaceutically" or "pharmaceutically acceptable" refer to molecular entities and compositions that do not produce an adverse, allergic or other untoward reaction when administered to an animal, or a human, as appropriate.

As used herein, "pharmaceutically acceptable excipient, vehicle or carrier" includes in particular diluents, adjuvants, excipients, or vehicles. The use of such ingredients for pharmaceutical active substances is well known in the art.

In the context of the invention, the term "treating" or "treatment", as used herein, means reversing, alleviating, inhibiting the progress of, or preventing the disorder or condition to which such term applies, or one or more symptoms of such disorder or condition.

"Therapeutically effective amount" means an amount of a compound/medicament according to the present invention effective in producing the desired therapeutic effect.

According to the invention, the term "patient", or "patient in need thereof", is intended for a human or non-human mammal affected or likely to be affected with the above disorders. Preferably, the patient is a human.

Compound (A) may administered in unit dosage forms, wherein the term "unit dose" means a single dose which is capable of being administered to a patient, and which can be readily handled and packaged, remaining as a physically and chemically stable unit dose comprising either the active compound itself, or as a pharmaceutically acceptable composition.

The appropriate unitary dosage forms comprise the oral forms; the sublingual, buccal, intratracheal, intraocular, intranasal forms, by inhalation, the topical, transdermal, sub-cutaneous, intramuscular or intra-venous, and the rectal forms and the implants.

The daily dose of between 10 and 90 µg according to the invention may be achieved by administering half a unit dosage form, a single unit dosage form or two or more unit dosage forms, according to the marketed unit dosage form, the daily dose to be administered and the frequency of administration that is prescribed by the practitioner.

Some salts of compound (A) are novel. According to another object, the present invention also concerns the following compounds per se:

(3S)-4-{4-[3-(3-methylpiperidin-1-yl)propoxy] phenyl}pyridine 1-oxide dihydrochloride tetrahydrate
(3S)-4-{4-[3-(3-methylpiperidin-1-yl)propoxy] phenyl}pyridine 1-oxide L-tartrate and its trihydrate;
(3S)-4-{4-[3-(3-methylpiperidin-1-yl)propoxy] phenyl}pyridine 1-oxide pamoate;
(3S)-4-{4-[3-(3-methylpiperidin-1-yl)propoxy] phenyl}pyridine 1-oxide fumarate;
(3S)-4-{4-[3-(3-methylpiperidin-1-yl)propoxy] phenyl}pyridine 1-oxide para-toluenesulfonate and its sestertihydrate (2.5)
(3S)-4-{4-[3-(3-methylpiperidin-1-yl)propoxy] phenyl}pyridine 1-oxide 1,5-naphtalenedisulfonate, and its hemiethanolate monohydrate;
(3S)-4-{4-[3-(3-methylpiperidin-1-yl)propoxy] phenyl}pyridine 1-oxide phosphate;
(3S)-4-{4-[3-(3-methylpiperidin-1-yl)propoxy] phenyl}pyridine 1-oxide bromhydrate;
(3S)-4-{4-[3-(3-methylpiperidin-1-yl)propoxy] phenyl}pyridine 1-oxide 1,2-ethanedisulfonate;
(3S)-4-{4-[3-(3-methylpiperidin-1-yl)propoxy] phenyl}pyridine 1-oxide sulfate;
(3S)-4-{4-[3-(3-methylpiperidin-1-yl)propoxy] phenyl}pyridine 1-oxide dibromhydrate;
(3S)-4-{4-[3-(3-methylpiperidin-1-yl)propoxy] phenyl}pyridine 1-oxide orotate and its dihydrate;
(3S)-4-{4-[3-(3-methylpiperidin-1-yl)propoxy] phenyl}pyridine 1-oxide 5-sulfosalicylate;
(3S)-4-{4-[3-(3-methylpiperidin-1-yl)propoxy] phenyl}pyridine 1-oxide 1-hydroxy-2-naphtoate and its monohydrate;
(3S)-4-{4-[3-(3-methylpiperidin-1-yl)propoxy] phenyl}pyridine 1-oxide 3-hydroxy-2-naphtoate;
(3S)-4-{4-[3-(3-methylpiperidin-1-yl)propoxy] phenyl}pyridine 1-oxide (sesqui)glycolate and its monohydrate.

DETAILED DESCRIPTION

The following examples are given for illustrative, non-limiting embodiments of the present invention.

EXAMPLES

Example 1

PK Results in Human $C_{max}$ of Compound (A) given orally once-a-day at doses of either 60 or 90 µg was reached about 2.5 to 3.5 h post administration at Day 1 and Day 10 with an average of 121 and 171 pg/mL after a single dose, and 172 and 344 pg/mL after repeated dose for 60 and 90 µg, respectively.

The activity of Compound (A) on vigilance at a dose as low as 30 µg daily was evidenced by a delay in falling asleep when going to bed at night whereas repeated treatment at 90 µg once-a-day for 10 days led to some insomnia.

The mean $t_{1/2}$ was about 33 h determined at Day 10 after multiple administrations. The total body clearance (Clss/F) was decreased by 65% and 74% after repeated dosing with 60 and 90 µg of Compound (A), respectively. The serum levels of Compound (A) after the 60 µg dose administration were higher after repeated dosing (Day 10) than after a single dose (Day 1) as reflected in a 42% higher $C_{max}$ and a 73% higher $AUC_{0-24\ h}$. The % accumulation after repeated administration was more marked for 90 µg dose with a 101% higher $C_{max}$ and a 113% higher $AUC_{0-24\ h}$.

Based on mean $C_{max}$ and $AUC_{0-24\ h}$ dose normalized ratios, Compound (A) serum exposure in human volunteers had a tendency to increase more than dose-proportionally between 60 and 90 µg o.d. between Day 1 and Day 10.

Steady state seems to be attained after 7 to 8 days of treatment for the 60 µg dose.

Example 2

Determination of the Active Dose of Compound (A)

The therapeutic activity of histamine H3-receptor antagonists/inverse agonists drugs can be predicted by evaluation of the degree of occupancy of their target in brain i.e. the H3 receptor.

This occupancy by drugs can be measured reliably in human through their displacing the binding of a selective radioactive probe, labelled with a radioisotope of short half-life like 11-C. In this way PET imaging allows for the non-invasive measurement of receptor occupancy. The process of imaging requires the injection of a positron-emitting radiotracer that binds to the receptor followed by the measurement of this binding using the PET scanner. Radioligands selective for the H3 receptor have been developed among which [$^{11}$C] GSK189254 is a histamine H3 receptor antagonist with a high affinity. It has good brain penetration and a terminal half-life of 1.6+0.4 hours. This tracer has been used recently to characterize the dose-response occupancy of novel histamine H3 antagonists, providing validation for the ability of [$^{11}$C]-GSK189254 to measure H3 receptors in humans using PET(Ashworth, S., et al., *Evaluation of 11C-GSK189254 as a novel radioligand for the H3 receptor in humans using PET.* J Nucl Med, 2010. 51(7): p. 1021-9).

This method allows to predict the therapeutic dose of a new H3 receptor inverse agonist/antagonist in two steps: 1/the degree of receptor occupancy associated with the dose ensuring therapeutic efficacy of a known drug A is determined, 2/the dose of the new drug B ensuring the same receptor occupancy as A at therapeutic dose is evaluated.

This strategy was applied by comparing H3R occupancy in healthy volunteers receiving pitolisant, an approved and marketed H3R inverse agonist, at its oral maximal therapeutic dose of 40 mg to occupancy by Compound (A) given at several dosages. H3R occupancy after 40 mg pitolisant in 6 healthy volunteers was found of 82,33±8.71%.

As shown below, very close H3R occupancy was found at a dose of 60 μg of Compound (A) and, at a dose of 30 μg of Compound (A) very high degree of occupancy was still present, particularly after treatment repeated once-a-day for 10 days when steady state is reached.

| Compound (A) dose | Percent H3R occupancy ± SD | |
|---|---|---|
| | at t$_{max}$ (3 h) | At through (24 h) |
| 30 μg once | −70.75 ± 2.94 | −46.50 ± 12.71 |
| 60 μg once | −82.00 ± 2.60 | |
| 60 μg repeated | −87.25 ± 3.6 | −75.50 ± 2.6 |

Since dose-response trials of pitolisant indicate therapeutic activity in various pathologies (narcolepsy, excessive daytime sleepiness associated with Parkinson's disease or Obstructive Sleep Apnea) at oral doses of 20 to 40 mg, the results above lead to the conclusion that the therapeutic dose of the Compound (A) is around 30 to 60 μg. Hence the latter compound appears 1,000-fold more potent than the marketed drug pitolisant.

Melting points are determined on Büchi capillary melting point apparatus.

Proton NMR spectra are recorded on a Varian 400 MHz NMR instrument. The chemical shifts δ are expressed in ppm. The following abbreviations are used to denote signal patterns: s=singlet, d=doublet, t=triplet, q=quadruplet, m=multiplet, ms=massif. The spectra recorded are consistent with the proposed structures.

Infrared spectra (range 4000-450 cm-1) are recorded on a THERMO Electron Corporation Nicolet 380 FT-IR equipped with an attenuated total reflection system. Wavelengths are in cm-1.

Example 3

(3S)-4-{4-[3-(3-Methylpiperidin-1-yl)propoxy]phenyl}pyridine 1-oxyde dihydrochloride tetrahydrate (3S)-4-{4-[3-(3-Methylpiperidin-1-yl)propoxy]phenyl}pyridine 1-oxyde dihydrochloride (210 g) and water (200 g) are charged in evaporation vessel. Temperature of bath in evaporation system is set to about 40° C. and mixture is agitated until all the precipitate is dissolved. Water is evaporated until product separates as solid form.

Evaporation vessel containing the product is transferred in vacuum tray drier and product is dried at 30° C. Product is transferred from evaporation vessel into actual drying vessel and drying is continued at 30° C. until water content of product is 15.3±0.5% in weight.

Example 4

(3S)-4-{4-[3-(3-methylpiperidin-1-yl)propoxy]phenyl}pyridine 1-oxide dihydrochloride tetrahydrate Acetone (10 kg) and (3S)-4-{4-[3-(3-methylpiperidin-1-yl)propoxy]phenyl}pyridine 1-oxyde (2.5 kg) are charged. Temperature is set at 30-40° C. The mixture is stirred until (3S)-4-{4-[3-(3-methylpiperidin-1-yl)propoxy]phenyl}pyridine 1-oxide dissolves, filtered through pressure filter, and concentrated. A solution of hydrochloric acid (32%, 1.84 kg, 2.1 equivalents) in water (2 kg) is added. Temperature is set to 22-30° C. and acetone (6 to 7 L) is added. After seeding acetone is added up to a total amount of 20 kg at 22-30° C. The suspension is agitated at 18-24° C. for 1-2 hours and filtered. The cake is rinsed with a mixture of acetone (3.5 kg) and water (240 g). product is dried in vacuum tray dryer with nitrogen flow (Tmax=30° C.) until water content is 15.0-16.5% in weight.

Example 5

(3S)-4-{4-[3-(3-methylpiperidin-1-yl)propoxy]phenyl}pyridine 1-oxide base (3S)-4-{4-[3-(3-methylpiperidin-1-yl)propoxy]phenyl}pyridine 1-oxide, dihydrochloride is treated with ethyl acetate, water, concentrated sodium hydroxide and potassium carbonate to free the base. The phases are filtered through a pad of celite and decantated. The organic phase is washed with saturated aqueous sodium chloride, dried over magnesium sulfate, filtered and concentrated under reduced pressure to yield (3S)-4-{4-[3-(3-methylpiperidin-1-yl)propoxy]phenyl}pyridine 1-oxide base. The crude base is refluxed in diisopropyl ether and let crystallize at room temperature. The obtained solid is filtered and dried at 40° C. under vacuum for 2 days to give pure (3S)-4-{4-[3-(3- methylpiperidin-1-yl)propoxy]phenyl}pyridine 1-oxide base as a white solid, melting at 91° C.

1H NMR (DMSO-d6): 8.17 (d,2H), 7.69 (d,2H), 7.68 (d,2H), 7.00 (d,2H), 4.02 (t,2H), 2.72 (m,2H), 2.35 (t, 2H), 1.90-1.70 (ms,3H), 1.65-1.35 (ms,5H), 0.85-0.75 (ms,4H).

IR (main bands): 2929, 2766, 1606, 1473, 1465, 1241, 1177, 1061, 1029, 822, 569, 515.

Example 6

(3S)-4-{4-[3-(3-methylpiperidin-1-yl)propoxy]phenyl}pyridine 1-oxide oxalate (3S)-4-{4-[3-(3-methylpiperidin-1-yl)propoxy]phenyl}pyridine 1-oxide base is dissolved in acetone and treated with a solution of one equivalent of oxalic acid in acetone. The obtained white suspension is stirred for 15 hours at room temperature, filtered, rinsed with acetone and dried at 40° C. under vacuum for 2 days to yield (3S)-4-{4-[3-(3-methylpiperidin-1-yl)propoxy]phenyl}pyridine 1-oxide oxalate as an off-white solid melting at 102° C.

1H NMR (D$_2$O): 8.12 (d,2H), 7.65 (d,2H), 7.58 (d,2H), 6.95 (d,2H), 4.06 (m,2H), 3.41 (m,1H), 3.34 (m,1H), 3.16 (m, 2H), 2.70 (t,1H), 2.43 (t,1H), 2.150 (m, 2H), 1.85-1.50 (ms,4H), 0.98 (m,1H), 0.79 (s,3H).

IR (main bands): 2963, 2501, 1704, 1602, 1470, 1449, 1409, 1391, 1287, 1256, 1225, 1169, 1052, 826, 815, 766, 695, 574, 449.

Example 7

(3S)-4-{4-[3-(3-methylpiperidin-1-yl)propoxy]phenyl}pyridine 1-oxide L-tartrate trihydrate (3S)-4-{4-[3-(3-methylpiperidin-1-yl)propoxy]phenyl}pyridine 1-oxide base is dissolved in ethanol and treated with a solution of one equivalent of L-tartaric acid in ethanol. The obtained white suspension is sonicated and then stirred for 15 hours at room temperature, filtered, rinsed with ethanol and dried at 45° C. under vacuum for 15 hours to yield (3S)-4-{4-[3-(3-methylpiperidin-1-yl)propoxy]phenyl}pyridine 1-oxide L-tartrate trihydrate as a white solid melting at 86° C.

1H NMR (D$_2$O): 8.19 (d,2H), 7.73 (d,2H), 7.66 (d,2H), 7.02 (d,2H), 4.40 (s,2H), 4.12 (m,2H), 3.46 (m,1H), 3.39 (m,1H), 3.21 (m, 2H), 2.75 (t,1H), 2.45 (t,1H), 2.15 (m, 2H), 1.89-1.61 (ms,4H), 1.05 (m,1H), 0.84 (s,3H).

IR (main bands): 2982, 2882, 2500, 1650, 1600, 1470, 1260, 1213, 1114, 1070, 1046, 883, 674, 576, 477.

Example 8

(3S)-4-{4-[3-(3-methylpiperidin-1-yl)propoxy]phenyl}pyridine 1-oxide pamoate (3S)-4-{4-[3-(3-methylpiperidin-1-yl)propoxy]phenyl}pyridine 1-oxide base and one equivalent of pamoic acid is refluxed in ethanol. The obtained yellow suspension is stirred for 15 hours at room temperature and filtered. The solid (which contains an excess of acid) is refluxed in ethanol, filtered while hot and the filtrate concentrated under reduced pressure then dissolved in a minimum of hot ethanol. Methyl tert-butylether is added to induce precipitation of the salt. After stirring at room temperature for 2 days, filtration, rinse with methyl tert-butylether and filtration the solid is dried at 45° C. under vacuum for 15 hours to yield (3S)-4-{4-[3-(3-methylpiperidin-1-yl) propoxy]phenyl}pyridine 1-oxide pamoate as a yellow solid melting at 179° C. 1H NMR (DMSO-d6): 8.24 (s,2H), 8.17 (d,2H), 8.14 (d,2H), 7.71-7.65 (ms,6H), 7.18 (m,2H), 7.06-7.01 (ms,4H), 4.69 (s,2H), 4.09 (t,2H), 2.77 (t,1H), 2.14 (m, 2H), 1.85-1.61 (ms,4H), 1.07 (m,1H), 0.88 (s,3H). Missing signals are hidden by deuterated solvent peaks.

IR (main bands): 2984, 2500, 1644, 1567, 1510, 1445, 1392, 1354, 1214, 1196, 810, 751, 596, 482, 401.

Example 9

(3S)-4-{4-[3-(3-methylpiperidin-1-yl)propoxy]phenyl}pyridine 1-oxide fumarate (3S)-4-{4-[3-(3-methylpiperidin-1-yl)propoxy]phenyl}pyridine 1-oxide base is dissolved in hot acetone and treated with a solution of one equivalent of fumaric acid in hot acetone. The obtained white gum is refluxed and then stirred for 15 hours at room temperature to give a white solid. After filtration, rinse with acetone and drying at 45° C. under vacuum for 15 hours (3S)-4-{4-[3-(3-methylpiperidin-1-yl)propoxy]phenyl}pyridine 1-oxide fumarate is obtained as a white solid melting at 135° C.

1H NMR (DMSO-d6): 8.18 (d,2H), 8.14 (d,2H), 7.70 (d,2H), 7.68 (d,2H), 7.01 (d,2H), 6.53 (s,2H), 4.04 (t,2H), 2.90 (m,2H), 2.56 (m, 2H), 2.06-1.85 (ms,3H), 1.75 (m,1H), 1.70-1.50 (ms,3H), 1.49 (m,1H), 0.88 (m,1H), 0.82 (s,3H).

IR (main bands): 3161, 2500, 1713, 1656, 1574, 1470, 1403, 1339, 1257, 1235, 1144, 1110 1038, 983, 918, 840, 790, 756, 627, 573, 454.

Example 10

(3S)-4-{4-[3-(3-methylpiperidin-1-yl)propoxy]phenyl}pyridine 1-oxide para-toluenesulfonate sestertihydrate (2.5)

A suspension of (3S)-4-{4-[3-(3-methylpiperidin-1-yl)propoxy]phenyl}pyridine 1-oxide base in water is treated with a solution of one equivalent of para-toluenesulfonic acid in water. The resulting homogeneous phase is lyophilized and let evolve at room temperature in open air for two days to yield (3S)-4-{4-[3-(3-methylpiperidin-1-yl)propoxy]phenyl}pyridine 1-oxide para-toluenesulfonate sestertihydrate as an off-white solid melting at 201° C.

1H NMR (D$_2$O): 8.10 (d,2H), 7.62 (d,2H), 7.55 (d,2H), 7.49 (d,2H), 7.17 (d,2H), 6.92 (d,2H), 4.40 (s,2H), 4.03 (t,2H), 3.37 (m,1H), 3.30 (m,1H), 3.14 (m,2H), 2.71 (m,1H), 2.44 (m,1H), 2.20 (s,3H), 2.06 (m, 2H), 1.85-1.50 (ms,4H), 1.00 (m,1H), 0.79 (s,3H).

IR (main bands): 2541, 2353, 1651, 1601, 1469, 1402, 1284, 1224, 1205, 1163, 1119, 1030, 1007, 943, 850, 820, 680, 628, 559, 521, 487.

Example 11

(3S)-4-{4-[3-(3-methylpiperidin-1-yl)propoxy]phenyl}pyridine 1-oxide 1,5-naphtalenedisulfonate monohydrate hemiethanolate A solution of (3S)-4-{4-[3-(3-methylpiperidin-1-yl)propoxy]phenyl}pyridine 1-oxide base in ethanol is treated with a solution of one equivalent of 1,5 naphtalene disulfonic acid in ethanol. The resulting suspension is stirred at room temperature for 15 hours, filtered, rinsed with ethanol and dried at 40° C. under vacuum for 2 days to yield (3S)-4-{4-[3-(3-methylpiperidin-1-yl)propoxy]

phenyl}pyridine 1-oxide 1,5-naphtalenedisulfonate monohydrate hemiethanolate as a white solid melting at 276° C.

1H NMR (D$_2$O): 8.65 (d,2H), 8.11 (d,2H), 8.00 (d,2H), 7.60 (d,2H), 7.53 (m,2H), 7.49 (m,2H), 6.86 (d,2H), 3.98 (t,2H), 3.37 (m,1H), 3.29 (m,1H), 3.09 (m,2H), 2.64 (t,1H), 2.36 (t,1H), 2.05 (m, 2H), 1.80-1.50 (ms,4H), 0.95 (m,1H), 0.77 (s,3H).

IR (main bands): 3026, 1601, 1487, 1416, 1261, 1213, 1114, 1030, 983, 806, 764, 665, 609, 580, 526, 502.

Example 12

(3S)-4-{4-[3-(3-methylpiperidin-1-yl)propoxy]phenyl}pyridine 1-oxide phosphate

A suspension of (3S)-4-{4-[3-(3-methylpiperidin-1-yl)propoxy]phenyl}pyridine 1-oxide base in water is treated with one equivalent of 85% phosphoric acid in water. The resulting homogeneous phase is lyophilized and let evolve at room temperature in open air for two days to yield (3S)-4-{4-[3-(3-methylpiperidin-1-yl)propoxy]phenyl}pyridine 1-oxide phosphate as a white solid melting at 116° C.

1H NMR (D$_2$O): 8.11 (d,2H), 7.64 (d,2H), 7.57 (d,2H), 6.95 (d,2H), 4.05 (m,2H), 3.42 (m,1H), 3.34 (m,1H), 3.15 (m, 2H), 2.70 (t,1H), 2.43 (t,1H), 2.10 (m, 2H), 1.85-1.50 (ms,4H), 0.99 (m,1H), 0.79 (s,3H).

IR (main bands): 2975, 2883, 2398, 2351, 1603, 1470, 1259, 1216, 1046, 932, 871, 812, 524, 502, 485, 450.

Example 13

(3S)-4-{4-[3-(3-methylpiperidin-1-yl)propoxy]phenyl}pyridine 1-oxide bromhydrate A solution of (3S)-4-{4-[3-(3-methylpiperidin-1-yl)propoxy]phenyl}pyridine 1-oxide base in tetrahydrofuran is treated with one equivalent of 48% bromhydric acid in water. The resulting suspension is stirred at room temperature for 15 hours, concentrated under reduced pressure and azeotroped with ethanol twice to yield a sticky solid. Dilution in hot acetonitrile, concentration under reduced pressure and drying at 40° C. under vacuum for 2 days afford (3S)-4-{4-[3-(3-methylpiperidin-1-yl)propoxy]phenyl}pyridine 1-oxide bromhydrate as a white solid melting at 76° C.

1H NMR (D$_2$O): 8.15 (d,2H), 7.68 (d,2H), 7.62 (d,2H), 6.98 (d,2H), 4.09 (t,2H), 3.44 (m,1H), 3.36 (m,1H), 3.18 (m, 2H), 2.72 (m,1H), 2.45 (m,1H), 2.13 (m, 2H), 1.85-1.55 (ms,4H), 1.05 (m,1H), 0.82 (s,3H).

IR (main bands): 3390, 2930, 2633, 2541, 2360, 1604, 1469, 1227, 1173, 1054, 1029, 945, 821, 568, 518, 487.

Example 14

(3S)-4-{4-[3-(3-methylpiperidin-1-yl)propoxy]phenyl}pyridine 1-oxide 1,2-ethanedisulfonate A suspension of (3S)-4-{4-[3-(3-methylpiperidin-1-yl)propoxy]phenyl}pyridine 1-oxide base in water is treated with a solution of one equivalent of 1,2 ethanedisulfonic acid in water. The resulting homogeneous phase is lyophilized and let evolve at room temperature in open air for two days to yield a hygroscopic solid. Trituration in tetrahydrofuran, filtration and drying at 40° C. under vacuum for 2 days give (3S)-4-{4-[3-(3-methylpiperidin-1-yl)propoxy]phenyl}pyridine 1-oxide 1,2-ethanedisulfonate as a beige solid melting at 155° C.

1H NMR (D$_2$O): 8.16 (d,2H), 7.69 (d,2H), 7.61 (d,2H), 6.98 (d,2H), 4.08 (t,2H), 3.44 (m,1H), 3.36 (m,1H), 3.18 (m, 2H), 2.72 (m,1H), 2.45 (t,1H), 2.12 (m, 2H), 1.85-1.55 (ms,4H), 1.02 (m,1H), 0.81 (s,3H).

IR (main bands): 3390, 2944, 2726, 2355, 1600, 1472, 1218, 1166, 1131, 1022, 997, 823, 760, 544, 524, 500.

Example 15

(3S)-4-{4-[3-(3-methylpiperidin-1-yl)propoxy]phenyl}pyridine 1-oxide sulfate

A suspension of (3S)-4-{4-[3-(3-methylpiperidin-1-yl)propoxy]phenyl}pyridine 1-oxide base in water is treated with one equivalent of aqueous 5N sulfuric acid. The resulting homogeneous phase is lyophilized and let evolve at room temperature in open air for two hours to yield (3S)-4-{4-[3-(3-methylpiperidin-1-yl)propoxy]phenyl}pyridine 1-oxide sulfate as an off-white solid melting at 71° C.

1H NMR (D$_2$O): 8.14 (d,2H), 7.67 (d,2H), 7.61 (d,2H), 6.97 (d,2H), 4.08 (t,2H), 3.42 (m,1H), 3.35 (m,1H), 3.18 (m, 2H), 2.73 (m,1H), 2.45 (m,1H), 2.12 (m, 2H), 1.85-1.55 (ms,4H), 1.03 (m,1H), 0.82 (s,3H).

IR (main bands): 3377, 2931, 2357, 1604, 1470, 1285, 1229, 1174, 1027, 945, 821, 602, 568, 518, 487.

Example 16

(3S)-4-{4-[3-(3-methylpiperidin-1-yl)propoxy]phenyl}pyridine 1-oxide dibromhydrate A solution of (3S)-4-{4-[3-(3-methylpiperidin-1-yl)propoxy]phenyl}pyridine 1-oxide base in ethanol is treated with two equivalents of aqueous 48% bromhydric acid in water. The resulting solution is precipitated with ethyl acetate and stirred at room temperature for 15 hours. After filtration, rinse with ethyl acetate and drying at 40° C. under vacuum for 15 hours (3S)-4-{4-[3-(3-methylpiperidin-1-yl)propoxy]phenyl}pyridine 1-oxide dibromhydrate is obtained as an off-white solid melting at 215° C.

1H NMR (D$_2$O): 8.24 (d,2H), 7.76 (d,2H), 7.67 (d,2H), 7.03 (d,2H), 4.13 (t,2H), 3.49 (m,1H), 3.41 (m,1H), 3.25 (m, 2H), 2.78 (m,1H), 2.50 (t,1H), 2.18 (m, 2H), 1.90-1.60 (ms,4H), 1.08 (m,1H), 0.87 (s,3H).

IR (main bands): 2930, 2632, 2352, 1601, 1471, 1410, 1292, 1261, 1210, 1182, 1050, 945, 823, 704, 678, 625, 569, 502, 485.

Example 17

(3S)-4-{4-[3-(3-methylpiperidin-1-yl)propoxy]phenyl}pyridine 1-oxide orotate dihydrate A suspension of (3S)-4-{4-[3-(3-methylpiperidin-1-yl)propoxy]phenyl}pyridine 1-oxide base in water is treated with a suspension of one equivalent of orotic acid in water. The resulting homogeneous phase is lyophilized and let evolve at room temperature in open air for 24 hours to yield (3S)-4-{4-[3-(3-methylpiperidin-1-yl)propoxy]phenyl}pyridine 1-oxide orotate dihydrate as a white solid melting at 125° C.

1H NMR (D$_2$O): 8.14 (d,2H), 7.66 (d,2H), 7.59 (d,2H), 6.95 (d,2H), 5.98 (s,1H), 4.07 (t,2H), 3.43 (m,1H), 3.36 (m,1H), 3.18 (m, 2H), 2.72 (m,1H), 2.45 (m,1H), 2.11 (m, 2H), 1.85-1.55 (ms,4H), 1.04 (m,1H), 0.82 (s,3H).

IR (main bands): 2957, 2789, 1667, 1633, 1605, 1472, 1409, 1355, 1285, 1226, 1176, 819, 765, 572, 539, 418.

Example 18

(3S)-4-{4-[3-(3-methylpiperidin-1-yl)propoxy]phenyl}pyridine 1-oxide 5-sulfosalicylate A solution of (3S)-4-{4-[3-(3-methylpiperidin-1-yl)propoxy]phenyl}pyridine 1-oxide base in ethanol is treated with a solution of one equivalent of 5-sulfosalicylic acid dihydrate in ethanol. The resulting suspension is stirred at room temperature for 20 hours, filtered, rinsed with ethanol and dried at 45° C. under vacuum for 24 hours to yield (3S)-4-{4-[3-(3-methylpiperidin-1-yl)propoxy]phenyl}pyridine 1-oxide 5-sulfosalicylate as a white solid melting at 213° C.

1H NMR ($D_2O$): 8.13 (d,2H), 8.06 (s,1H), 7.67 (d,1H), 7.63 (d,2H), 7.53 (d,2H), 6.90 (d,2H), 6.86 (d,2H), 4.04 (m,2H), 3.42 (m,1H), 3.34 (m,1H), 3.16 (m, 2H), 2.70 (m,1H), 2.43 (m,1H), 2.09 (m, 2H), 1.85-1.55 (ms,4H), 1.02 (m,1H), 0.81 (s,3H).

IR (main bands): 2963, 2671, 2556, 2358, 1667, 1602, 1471, 1366, 1290, 1240, 1164, 1149, 1117, 1021, 878, 771, 667, 584, 503.

Example 19

(3S)-4-{4-[3-(3-methylpiperidin-1-yl)propoxy]phenyl}pyridine 1-oxide 1-hydroxy-2-naphtoate monohydrate A solution of (3S)-4-{4-[3-(3-methylpiperidin-1-yl)propoxy]phenyl}pyridine 1-oxide base in ethanol is treated with a solution of one equivalent of 1-hydroxy-2-naphtoic acid in ethanol and water. The resulting homogeneous phase is lyophilized and let evolve at room temperature in open air for 24 hours to yield (3S)-4-{4-[3-(3-methylpiperidin-1-yl)propoxy]phenyl}pyridine 1-oxide 1-hydroxy-2-naphtoate monohydrate as a beige solid melting at 140° C.

1H NMR (DMSO-d6): 8.18 (d,2H), 8.15 (m,1H), 7.75-7.65 (ms,6H), 7.43 (m,1H), 7.35 (m,1H), 7.01 (d,2H), 6.97 (d,2H), 4.08 (t,2H), 3.10 (m,2H), 2.60 (m,1H), 2.10 (m, 2H), 1.85-1.60 (ms,4H), 1.02 (m,1H), 0.87 (s,3H). Missing signals are hidden by deuterated solvent peaks.

IR (main bands): 3500, 2356, 1609, 1580, 1471, 1402, 1367, 1313, 1239, 1175, 1035, 984, 806, 774, 578, 491, 447, 426.

Example 20

(3S)-4-{4-[3-(3-methylpiperidin-1-yl)propoxy]phenyl}pyridine 1-oxide 3-hydroxy-2-naphtoate A solution of (3S)-4-{4-[3-(3-methylpiperidin-1-yl)propoxy]phenyl}pyridine 1-oxide base in ethanol is treated with a solution of one equivalent of 3-hydroxy-2-naphtoic acid in ethanol. The resulting homogeneous phase is concentrated under reduced pressure to yield an oily residue. Acetone is then added and the solution concentrated under reduced pressure to yield a yellow solid. A minimum of acetone and a drop of water are added and the resulting suspension sonicated and stirred at room temperature for 20 hours. Filtration, rinse with acetone and drying under vacuum at 45° C. for 24 hours yield (3S)-4-{4-[3-(3-methylpiperidin-1-yl)propoxy]phenyl}pyridine 1-oxide 3-hydroxy-2-naphtoate as an off-white solid melting at 199° C.

1H NMR (DMSO-d6): 8.26 (s,1H), 8.18 (d,2H), 7.72 (d,1H), 7.70-7.65 (ms,4H), 7.56 (d,2H), 7.31 (t,1H), 7.13 (t,1H), 7.01 (d,2H), 6.94 (s,1H), 4.08 (t,2H), 3.11 (m,2H), 2.64 (m,1H), 2.11 (m, 2H), 1.85-1.60 (ms,4H), 1.02 (m,1H), 0.87 (s,3H). Missing signals are hidden by deuterated solvent peaks.

IR (main bands): 2931, 2355, 1645, 1603, 1519, 1464, 1446, 1351, 1238, 1173, 841, 818, 739, 594, 577, 478.

Example 21

(3S)-4-{4-[3-(3-methylpiperidin-1-yl)propoxy]phenyl}pyridine 1-oxide sesquiglycolate monohydrate A solution of (3S)-4-{4-[3-(3-methylpiperidin-1-yl)propoxy]phenyl}pyridine 1-oxide base in tetrahydrofuran is treated with a solution of one equivalent of glycolic acid in tetrahydrofuran. The resulting suspension is stirred at room temperature for 24 hours. Filtration, rinse with tetrahydrofuran and drying under vacuum at 45° C. for 24 hours yield (3S)-4-{4-[3-(3-methylpiperidin-1-yl)propoxy]phenyl}pyridine 1-oxide sesquiglycolate monohydrate as an off-white solid melting at 82° C.

1H NMR ($D_2O$): 8.19 (d,2H), 7.71 (d,2H), 7.65 (d,2H), 7.01 (d,2H), 4.12 (t,2H), 3.48 (m,1H), 3.41 (m,1H), 3.22 (m, 2H), 2.76 (m,1H), 2.49 (t,1H), 2.17 (m, 2H), 1.90-1.60 (ms,4H), 1.06 (m,1H), 0.86 (s,3H).

IR (main bands): 3258, 3102, 2930, 2356, 1603, 1470, 1411, 1287, 1232, 1177, 1059, 947, 819, 696, 568, 509, 456.

Example 22

Comparative Pharmacokinetic Data in Mice

Compounds were administered to male swiss mice at a dose close to 1 mg of base/kg. Sampling was performed on a 24 hours time for plasma and brain. Results are presented in Table 1 with normalization at 1 mg of base/kg.

TABLE 1 pharmacokinetic data of the exemplified compounds

| example | AUC (ng/mg*hr) | |
|---|---|---|
| | plasma | brain |
| Example 5 | 769 | 860 |
| Example 6 | 562 | 923 |
| Example 4 | 619 | 1039 |
| Example 7 | 447 | 814 |
| Example 8 | 587 | 952 |
| Example 9 | 448 | 882 |
| Example 10 | 718 | 862 |
| Example 11 | 453 | 812 |
| Example 12 | 350 | 630 |
| Example 13 | 395 | 565 |
| Example 14 | 438 | 676 |
| Example 15 | 466 | 639 |
| Example 16 | 357 | 474 |
| Example 17 | 389 | 529 |
| Example 18 | 400 | 513 |
| Example 19 | 393 | 528 |
| Example 20 | 388 | 467 |
| Example 21 | 348 | 484 |

To some extent, the exemplified compounds display similar rates of absorption. Ratios of the AUC of the examples over the AUC of the dihydrochloride tetrahydrate are displayed in Table 2. The ratios all fit within the interval 0.6 to 1.2 which is relevant for similarity with respect to experimental errors associated with the test.

TABLE 2 comparison of the plasma AUC

| example | ratio |
|---|---|
| Example 5 | 1.2 |
| Example 6 | 0.9 |
| Example 4 | 1.0 |
| Example 7 | 0.7 |
| Example 8 | 0.9 |
| Example 9 | 0.7 |
| Example 10 | 1.2 |
| Example 11 | 0.7 |
| Example 12 | 0.6 |
| Example 13 | 0.6 |
| Example 14 | 0.7 |
| Example 15 | 0.8 |
| Example 16 | 0.6 |
| Example 17 | 0.6 |
| Example 18 | 0.6 |
| Example 19 | 0.6 |
| Example 20 | 0.6 |
| Example 21 | 0.6 |

Striking result is the one from the pamoate (Example 8). The pamoate (embonate) salts are generally used for making slow release drugs (See for example zypadhera/zyprexa relprevv the pamoate of olanzapine which is only given every two to four weeks). Example 8 shows similar AUC and similar time to reach Cmax when compared to the dihydrochloride tetrahydrate (Example 4).

The compound A as presently claimed thus allows a low dosage, irrespective of its salts and:or solvates therefrom.

Example 23

XRPD of (3S)-4-{4-[3-(3-methylpiperidin-1-yl)propoxy]phenyl}pyridine 1-oxide L-tartrate

| Angle 2-Theta ° | d value Angstrom | Intensity Count | Intensity % |
|---|---|---|---|
| 10.622 | 8.32195 | 1103 | 1.7 |
| 11.815 | 7.48397 | 65935 | 100 |
| 14.195 | 6.23436 | 21253 | 32.2 |
| 14.523 | 6.09411 | 2936 | 4.5 |
| 15.153 | 5.84212 | 1283 | 1.9 |
| 15.434 | 5.73636 | 804 | 1.2 |
| 16.086 | 5.50553 | 1990 | 3 |
| 16.205 | 5.46533 | 1154 | 1.7 |
| 16.543 | 5.35441 | 2062 | 3.1 |
| 16.731 | 5.2947 | 4284 | 6.5 |
| 18.055 | 4.90925 | 9130 | 13.8 |
| 18.695 | 4.74257 | 1523 | 2.3 |
| 19.319 | 4.59073 | 3270 | 5 |
| 19.675 | 4.50851 | 34400 | 52.2 |
| 20.425 | 4.34473 | 1578 | 2.4 |
| 21.416 | 4.14573 | 2992 | 4.5 |
| 22.083 | 4.02212 | 6703 | 10.2 |
| 22.785 | 3.89966 | 1791 | 2.7 |
| 23.396 | 3.79927 | 9372 | 14.2 |
| 23.634 | 3.76141 | 6562 | 10 |
| 24.514 | 3.62836 | 4959 | 7.5 |
| 24.614 | 3.61395 | 6019 | 9.1 |
| 24.985 | 3.56111 | 4404 | 6.7 |
| 25.261 | 3.52277 | 10605 | 16.1 |
| 26.032 | 3.42021 | 4443 | 6.7 |
| 26.383 | 3.37547 | 4383 | 6.6 |
| 27.058 | 3.29282 | 3008 | 4.6 |
| 27.855 | 3.20034 | 4765 | 7.2 |
| 28.226 | 3.15911 | 929 | 1.4 |
| 28.716 | 3.10633 | 815 | 1.2 |
| 31.766 | 2.81465 | 857 | 1.3 |
| 30.996 | 2.88282 | 525 | 0.8 |

Example 24

XRPD of (3S)-4-{4-[3-(3-methylpiperidin-1-yl)propoxy]phenyl}pyridine 1-oxide pamoate

| Angle 2-Theta ° | d value Angstrom | Intensity Count | Intensity % |
|---|---|---|---|
| 5.74 | 15.38566 | 5136 | 25.9 |
| 6.409 | 13.77904 | 4797 | 24.2 |
| 6.832 | 12.92799 | 4537 | 22.8 |
| 8.57 | 10.3099 | 3843 | 19.4 |
| 8.999 | 9.81895 | 4646 | 23.4 |
| 9.605 | 9.20102 | 13254 | 66.7 |
| 9.99 | 8.84695 | 8769 | 44.2 |
| 11.314 | 7.81432 | 6689 | 33.7 |
| 11.516 | 7.67772 | 7979 | 40.2 |
| 11.849 | 7.46299 | 3230 | 16.3 |
| 14.738 | 6.00572 | 15601 | 78.6 |
| 15.776 | 5.6129 | 11553 | 58.2 |
| 17.6 | 5.03509 | 2409 | 12.1 |
| 18.051 | 4.91034 | 2694 | 13.6 |
| 18.829 | 4.70924 | 3321 | 16.7 |
| 18.971 | 4.6741 | 4602 | 23.2 |
| 19.087 | 4.64614 | 5624 | 28.3 |
| 19.621 | 4.5207 | 4491 | 22.6 |
| 20.044 | 4.42624 | 19857 | 100 |
| 20.962 | 4.23449 | 3648 | 18.4 |
| 21.471 | 4.13528 | 2728 | 13.7 |
| 23.446 | 3.79125 | 6076 | 30.6 |
| 23.724 | 3.74742 | 11594 | 58.4 |
| 24.432 | 3.64041 | 2329 | 11.7 |
| 25.084 | 3.54727 | 4040 | 20.3 |
| 25.333 | 3.51291 | 3953 | 19.9 |
| 25.814 | 3.44857 | 4063 | 20.5 |
| 26.463 | 3.36542 | 9057 | 45.6 |
| 27.088 | 3.28922 | 4364 | 22 |
| 29.486 | 3.02694 | 2704 | 13.6 |
| 29.637 | 3.01185 | 3246 | 16.3 |
| 30.105 | 2.9661 | 6383 | 32.1 |
| 30.719 | 2.90813 | 2487 | 12.5 |

Example 25

XRPD of (3S)-4-{4-[3-(3-methylpiperidin-1-yl)propoxy]phenyl}pyridine 1-oxide fumarate

| Angle 2-Theta ° | d value Angstrom | Intensity Count | Intensity % |
|---|---|---|---|
| 7.379 | 11.97131 | 9660 | 42.2 |
| 10.544 | 8.38328 | 2567 | 11.2 |
| 10.821 | 8.16977 | 4686 | 20.5 |
| 11.069 | 7.98684 | 11911 | 52 |
| 11.442 | 7.72714 | 2661 | 11.6 |
| 12.41 | 7.12691 | 2199 | 9.6 |
| 12.642 | 6.99664 | 4495 | 19.6 |
| 12.893 | 6.86064 | 9427 | 41.1 |
| 13.265 | 6.66933 | 3425 | 14.9 |
| 14.807 | 5.97805 | 8722 | 38.1 |

-continued

| Angle 2-Theta ° | d value Angstrom | Intensity Count | Intensity % |
|---|---|---|---|
| 15.243 | 5.80815 | 22909 | 100 |
| 16.761 | 5.28508 | 5012 | 21.9 |
| 17.523 | 5.05717 | 3554 | 15.5 |
| 17.629 | 5.02701 | 2430 | 10.6 |
| 18.163 | 4.88022 | 4355 | 19 |
| 18.457 | 4.80316 | 3981 | 17.4 |
| 18.697 | 4.74204 | 4875 | 21.3 |
| 19.043 | 4.65678 | 4965 | 21.7 |
| 19.58 | 4.53026 | 3167 | 13.8 |
| 20.355 | 4.35932 | 3559 | 15.5 |
| 20.701 | 4.28734 | 4613 | 20.1 |
| 21.231 | 4.18149 | 2619 | 11.4 |
| 21.686 | 4.09481 | 6203 | 27.1 |
| 21.78 | 4.0773 | 8303 | 36.2 |
| 22.083 | 4.02208 | 3892 | 17 |
| 22.497 | 3.94889 | 4153 | 18.1 |
| 22.912 | 3.87837 | 6378 | 27.8 |
| 23.273 | 3.81905 | 2879 | 12.6 |
| 23.628 | 3.76242 | 3160 | 13.8 |
| 24.056 | 3.69642 | 3078 | 13.4 |
| 24.673 | 3.60534 | 5099 | 22.3 |
| 25.749 | 3.45709 | 3993 | 17.4 |
| 26.263 | 3.39054 | 3935 | 17.2 |
| 26.371 | 3.37691 | 3257 | 14.2 |
| 28.371 | 3.14324 | 3205 | 14 |

Example 26

XRPD of (3S)-4-{4-[3-(3-methylpiperidin-1-yl)propoxy]phenyl}pyridine 1-oxide para-toluenesulfonate

| Angle 2-Theta ° | d value Angstrom | Intensity Count | Intensity % |
|---|---|---|---|
| 8.126 | 10.87193 | 1220 | 4.3 |
| 8.672 | 10.18799 | 6320 | 22.5 |
| 13.043 | 6.782 | 1515 | 5.4 |
| 13.486 | 6.56057 | 2082 | 7.4 |
| 13.656 | 6.47898 | 2341 | 8.3 |
| 14.21 | 6.22769 | 1138 | 4 |
| 14.806 | 5.97829 | 2474 | 8.8 |
| 15.73 | 5.62906 | 8864 | 31.5 |
| 16.164 | 5.479 | 2933 | 10.4 |
| 16.903 | 5.24124 | 3707 | 13.2 |
| 17.419 | 5.08696 | 2268 | 8.1 |
| 18.628 | 4.75947 | 4913 | 17.5 |
| 19.312 | 4.59241 | 15833 | 56.3 |
| 20.289 | 4.37334 | 19600 | 69.6 |
| 20.797 | 4.26778 | 28145 | 100 |
| 21.268 | 4.17435 | 2009 | 7.1 |
| 21.599 | 4.11104 | 1072 | 3.8 |
| 22.363 | 3.97233 | 5381 | 19.1 |
| 22.629 | 3.92615 | 3120 | 11.1 |
| 22.912 | 3.87837 | 1881 | 6.7 |
| 23.649 | 3.75905 | 3082 | 10.9 |
| 23.714 | 3.74893 | 3090 | 11 |
| 24.37 | 3.64951 | 2706 | 9.6 |
| 25.812 | 3.44881 | 2104 | 7.5 |
| 26.505 | 3.36022 | 2945 | 10.5 |
| 27.153 | 3.28146 | 3658 | 13 |
| 27.541 | 3.23608 | 2573 | 9.1 |
| 27.781 | 3.20865 | 2650 | 9.4 |
| 28.673 | 3.11083 | 1953 | 6.9 |
| 28.92 | 3.0849 | 1536 | 5.5 |
| 29.771 | 2.99854 | 2149 | 7.6 |
| 29.939 | 2.98218 | 2140 | 7.6 |
| 30.581 | 2.92095 | 1503 | 5.3 |

Example 27

XRPD of (3S)-4-{4-[3-(3-methylpiperidin-1-yl)propoxy]phenyl}pyridine 1-oxide 1,5-naphtalenedisulfonate

| Angle 2-Theta ° | d value Angstrom | Intensity Count | Intensity % |
|---|---|---|---|
| 6.053 | 14.58946 | 3344 | 7.1 |
| 6.743 | 13.09747 | 9176 | 19.6 |
| 7.78 | 11.35388 | 1471 | 3.1 |
| 7.997 | 11.04653 | 7287 | 15.5 |
| 8.406 | 10.51039 | 1386 | 3 |
| 8.748 | 10.10043 | 761 | 1.6 |
| 9.024 | 9.7917 | 711 | 1.5 |
| 9.384 | 9.4165 | 4822 | 10.3 |
| 10.155 | 8.70326 | 2479 | 5.3 |
| 12.492 | 7.08029 | 2090 | 4.5 |
| 12.861 | 6.87769 | 9724 | 20.8 |
| 13.021 | 6.79386 | 9299 | 19.8 |
| 13.648 | 6.48297 | 988 | 2.1 |
| 13.911 | 6.36085 | 4282 | 9.1 |
| 14.206 | 6.22946 | 8003 | 17.1 |
| 14.563 | 6.07743 | 14657 | 31.3 |
| 14.884 | 5.94722 | 3561 | 7.6 |
| 15.519 | 5.70533 | 7539 | 16.1 |
| 15.997 | 5.53579 | 13027 | 27.8 |
| 16.693 | 5.30644 | 6992 | 14.9 |
| 16.97 | 5.22063 | 8861 | 18.9 |
| 17.171 | 5.1598 | 3936 | 8.4 |
| 17.374 | 5.10017 | 7022 | 15 |
| 18.039 | 4.91345 | 1201 | 2.6 |
| 18.571 | 4.77386 | 3537 | 7.5 |
| 18.888 | 4.69447 | 27322 | 58.3 |
| 19.086 | 4.64637 | 4783 | 10.2 |
| 19.807 | 4.47874 | 1710 | 3.6 |
| 20.286 | 4.37401 | 6783 | 14.5 |
| 20.494 | 4.33024 | 4507 | 9.6 |
| 20.919 | 4.24316 | 7847 | 16.7 |
| 21.599 | 4.11104 | 4775 | 10.2 |
| 21.875 | 4.05972 | 1370 | 2.9 |
| 22.84 | 3.8904 | 12628 | 26.9 |
| 23.389 | 3.8004 | 2704 | 5.8 |
| 23.971 | 3.70929 | 3139 | 6.7 |
| 24.146 | 3.68284 | 46862 | 100 |
| 24.829 | 3.58314 | 3736 | 8 |
| 24.978 | 3.56206 | 5320 | 11.4 |
| 25.394 | 3.50459 | 3987 | 8.5 |
| 25.9 | 3.43725 | 1812 | 3.9 |
| 26.371 | 3.37699 | 6140 | 13.1 |
| 27.04 | 3.29487 | 16001 | 34.1 |
| 29.238 | 3.05198 | 1261 | 2.7 |
| 29.689 | 3.00669 | 1091 | 2.3 |
| 31.068 | 2.87632 | 885 | 1.9 |

Example 28

XRPD of (3S)-4-{4-[3-(3-methylpiperidin-1-yl)propoxy]phenyl}pyridine 1-oxide phosphate

| Angle 2-Theta ° | d value Angstrom | Intensity Count | Intensity % |
|---|---|---|---|
| 6.479 | 13.6312 | 632 | 0.9 |
| 7.199 | 12.26997 | 71454 | 100 |
| 7.919 | 11.15605 | 5719 | 8 |
| 8.126 | 10.87193 | 3362 | 4.7 |
| 10.831 | 8.16165 | 54565 | 76.4 |
| 11.82 | 7.48098 | 2027 | 2.8 |
| 13.444 | 6.5806 | 1147 | 1.6 |
| 14.479 | 6.11247 | 12840 | 18 |
| 15.309 | 5.78298 | 828 | 1.2 |

-continued

| Angle 2-Theta ° | d value Angstrom | Intensity Count | Intensity % |
|---|---|---|---|
| 17.001 | 5.21115 | 2216 | 3.1 |
| 18.702 | 4.74095 | 2239 | 3.1 |
| 19.319 | 4.59078 | 1051 | 1.5 |
| 19.785 | 4.48366 | 1969 | 2.8 |
| 19.886 | 4.46122 | 1099 | 1.5 |
| 20.029 | 4.42972 | 1024 | 1.4 |
| 20.632 | 4.30154 | 673 | 0.9 |
| 21.141 | 4.19901 | 546 | 0.8 |
| 21.658 | 4.09993 | 2586 | 3.6 |
| 22.714 | 3.91164 | 2414 | 3.4 |
| 22.886 | 3.88275 | 1299 | 1.8 |
| 23.374 | 3.80267 | 1359 | 1.9 |

Example 29

XRPD of (3S)-4-{4-[3-(3-methylpiperidin-1-yl)propoxy]phenyl}pyridine 1-oxide bromhydrate phase A

| Angle 2-Theta ° | d value Angstrom | Intensity Count | Intensity % |
|---|---|---|---|
| 7.366 | 11.99193 | 3142 | 16.5 |
| 10.083 | 8.76605 | 8965 | 47.1 |
| 10.314 | 8.56959 | 4251 | 22.4 |
| 10.682 | 8.27515 | 2574 | 13.5 |
| 10.976 | 8.05473 | 15003 | 78.9 |
| 12.824 | 6.89744 | 1589 | 8.4 |
| 13.081 | 6.76278 | 1596 | 8.4 |
| 13.171 | 6.7164 | 1628 | 8.6 |
| 14.168 | 6.24609 | 3950 | 20.8 |
| 14.616 | 6.05576 | 14499 | 76.2 |
| 15.195 | 5.82609 | 6833 | 35.9 |
| 15.726 | 5.63059 | 2119 | 11.1 |
| 16.511 | 5.36452 | 2974 | 15.6 |
| 16.771 | 5.28195 | 2759 | 14.5 |
| 16.929 | 5.23308 | 2462 | 12.9 |
| 17.592 | 5.03747 | 1616 | 8.5 |
| 18.377 | 4.82405 | 4106 | 21.6 |
| 19.131 | 4.6355 | 7769 | 40.9 |
| 20.126 | 4.40844 | 3962 | 20.8 |
| 20.573 | 4.31372 | 3258 | 17.1 |
| 21.923 | 4.0511 | 19018 | 100 |
| 26.172 | 3.40217 | 14595 | 76.7 |
| 26.863 | 3.31621 | 4859 | 25.5 |
| 31.199 | 2.86449 | 9683 | 50.9 |

Example 30

XRPD of (3S)-4-{4-[3-(3-methylpiperidin-1-yl)propoxy]phenyl}pyridine 1-oxide bromhydrate phase B

| Angle 2-Theta ° | d value Angstrom | Intensity Count | Intensity % |
|---|---|---|---|
| 6.744 | 13.09621 | 1050 | 1.8 |
| 7.228 | 12.2209 | 1932 | 3.2 |
| 8.673 | 10.18673 | 12130 | 20.3 |
| 9.849 | 8.97367 | 8381 | 14 |
| 10.514 | 8.40736 | 17844 | 29.9 |
| 10.89 | 8.11809 | 642 | 1.1 |
| 11.392 | 7.76128 | 8500 | 14.2 |
| 11.995 | 7.37228 | 1390 | 2.3 |
| 13.032 | 6.78819 | 1501 | 2.5 |
| 13.413 | 6.59598 | 9133 | 15.3 |
| 13.759 | 6.43071 | 4006 | 6.7 |
| 14.403 | 6.14466 | 40322 | 67.5 |
| 16.315 | 5.42855 | 3092 | 5.2 |
| 17.128 | 5.17278 | 6865 | 11.5 |
| 17.448 | 5.07871 | 21423 | 35.9 |
| 17.918 | 4.94657 | 23891 | 40 |
| 18.528 | 4.78494 | 3852 | 6.5 |
| 19.482 | 4.55284 | 760 | 1.3 |
| 19.87 | 4.46475 | 8806 | 14.7 |
| 20.097 | 4.41485 | 59707 | 100 |
| 21.743 | 4.08418 | 12279 | 20.6 |
| 21.888 | 4.05736 | 30357 | 50.8 |
| 22.782 | 3.90019 | 6438 | 10.8 |
| 23.672 | 3.75554 | 962 | 1.6 |
| 24.002 | 3.70461 | 7607 | 12.7 |
| 24.678 | 3.60464 | 3017 | 5.1 |
| 25.006 | 3.55819 | 4063 | 6.8 |
| 26.367 | 3.37752 | 17805 | 29.8 |
| 26.962 | 3.30427 | 7319 | 12.3 |
| 27.265 | 3.26825 | 3138 | 5.3 |
| 27.894 | 3.19596 | 6098 | 10.2 |
| 28.171 | 3.1651 | 3293 | 5.5 |
| 29.188 | 3.05709 | 2873 | 4.8 |
| 29.933 | 2.98271 | 956 | 1.6 |
| 30.305 | 2.94696 | 625 | 1 |
| 30.661 | 2.91352 | 1732 | 2.9 |
| 31.203 | 2.86414 | 10127 | 17 |
| 31.479 | 2.83963 | 4690 | 7.9 |
| 31.885 | 2.80442 | 1430 | 2.4 |

Example 31

XRPD of (3S)-4-{4-[3-(3-methylpiperidin-1-yl)propoxy]phenyl}pyridine 1-oxide 1,2-ethanedisulfonate

| Angle 2-Theta ° | d value Angstrom | Intensity Count | Intensity % |
|---|---|---|---|
| 6.076 | 14.53457 | 2470 | 3.9 |
| 7.191 | 12.28301 | 1088 | 1.7 |
| 7.912 | 11.16587 | 63580 | 100 |
| 8.915 | 9.91132 | 1306 | 2.1 |
| 10.515 | 8.40664 | 1685 | 2.7 |
| 11.567 | 7.64396 | 23675 | 37.2 |
| 12.114 | 7.30033 | 16226 | 25.5 |
| 12.328 | 7.17374 | 1378 | 2.2 |
| 12.883 | 6.8659 | 1225 | 1.9 |
| 14.001 | 6.32031 | 1401 | 2.2 |
| 14.203 | 6.23063 | 1507 | 2.4 |
| 14.621 | 6.05375 | 12806 | 20.1 |
| 15.457 | 5.72797 | 1808 | 2.8 |
| 15.753 | 5.6209 | 34565 | 54.4 |
| 16.208 | 5.46428 | 995 | 1.6 |
| 16.683 | 5.30977 | 22245 | 35 |
| 17.275 | 5.12924 | 3929 | 6.2 |
| 17.73 | 4.99852 | 4056 | 6.4 |
| 17.999 | 4.9245 | 8781 | 13.8 |
| 18.866 | 4.69994 | 33732 | 53.1 |
| 19.029 | 4.66019 | 16126 | 25.4 |
| 19.507 | 4.54702 | 11670 | 18.4 |
| 20.333 | 4.36405 | 5760 | 9.1 |
| 20.543 | 4.31997 | 4220 | 6.6 |
| 21.136 | 4.20011 | 32904 | 51.8 |
| 22.152 | 4.00969 | 7803 | 12.3 |
| 22.369 | 3.97133 | 26731 | 42 |
| 23.257 | 3.82154 | 8128 | 12.8 |
| 23.485 | 3.78505 | 26515 | 41.7 |
| 23.741 | 3.74477 | 24996 | 39.3 |
| 24.363 | 3.65057 | 4500 | 7.1 |

-continued

| Angle 2-Theta ° | d value Angstrom | Intensity Count | Intensity % |
|---|---|---|---|
| 25.216 | 3.52896 | 1605 | 2.5 |
| 26.199 | 3.39876 | 2022 | 3.2 |
| 26.4 | 3.37332 | 1808 | 2.8 |
| 27.127 | 3.28459 | 2074 | 3.3 |
| 28.374 | 3.14301 | 12166 | 19.1 |
| 29.061 | 3.07018 | 899 | 1.4 |
| 29.374 | 3.03823 | 2634 | 4.1 |
| 29.486 | 3.02694 | 2110 | 3.3 |
| 30.02 | 2.97426 | 2448 | 3.9 |
| 30.518 | 2.92685 | 3091 | 4.9 |
| 30.996 | 2.88282 | 1407 | 2.2 |
| 31.384 | 2.84805 | 1061 | 1.7 |
| 31.609 | 2.8283 | 847 | 1.3 |
| 31.962 | 2.79787 | 1459 | 2.3 |

Example 32

XRPD of (3S)-4-{4-[3-(3-methylpiperidin-1-yl)propoxy]phenyl}pyridine 1-oxide sulfate phase A

| Angle 2-Theta ° | d value Angstrom | Intensity Count | Intensity % |
|---|---|---|---|
| 6.656 | 13.26963 | 2744 | 19.2 |
| 7.161 | 12.33535 | 2286 | 16 |
| 7.46 | 11.84024 | 6576 | 46 |
| 9.95 | 8.88266 | 2999 | 21 |
| 11.175 | 7.91137 | 5640 | 39.4 |
| 11.511 | 7.68092 | 2387 | 16.7 |
| 13.438 | 6.58388 | 4784 | 33.4 |
| 14.105 | 6.27406 | 2251 | 15.7 |
| 14.971 | 5.9127 | 2505 | 17.5 |
| 15.074 | 5.87279 | 2830 | 19.8 |
| 15.963 | 5.54771 | 3902 | 27.3 |
| 16.405 | 5.3991 | 3514 | 24.6 |
| 16.749 | 5.28906 | 10566 | 73.8 |
| 18.628 | 4.75947 | 2239 | 15.6 |
| 19.694 | 4.50416 | 14309 | 100 |
| 20.244 | 4.38303 | 9373 | 65.5 |
| 21.055 | 4.21607 | 2762 | 19.3 |
| 23.179 | 3.83432 | 9224 | 64.5 |
| 23.568 | 3.77192 | 3028 | 21.2 |
| 26.813 | 3.32229 | 3858 | 27 |
| 29.312 | 3.04443 | 3593 | 25.1 |

Example 33

XRPD of (3S)-4-{4-[3-(3-methylpiperidin-1-yl)propoxy]phenyl}pyridine 1-oxide sulfate phase B

| Angle 2-Theta ° | d value Angstrom | Intensity Count | Intensity % |
|---|---|---|---|
| 7.208 | 12.25347 | 15062 | 100 |
| 7.567 | 11.67291 | 6023 | 40 |
| 11.312 | 7.81562 | 8017 | 53.2 |
| 11.93 | 7.41239 | 4515 | 30 |
| 14.186 | 6.23803 | 3984 | 26.5 |
| 14.934 | 5.92757 | 5282 | 35.1 |
| 15.143 | 5.84614 | 3131 | 20.8 |
| 16.904 | 5.24091 | 7584 | 50.4 |
| 17.18 | 5.15723 | 1304 | 8.7 |
| 17.663 | 5.01733 | 10940 | 72.6 |
| 17.943 | 4.93966 | 2540 | 16.9 |
| 18.285 | 4.84791 | 1930 | 12.8 |

-continued

| Angle 2-Theta ° | d value Angstrom | Intensity Count | Intensity % |
|---|---|---|---|
| 19.51 | 4.54637 | 2589 | 17.2 |
| 20.389 | 4.35229 | 3820 | 25.4 |
| 20.703 | 4.28689 | 2852 | 18.9 |
| 20.979 | 4.23104 | 6185 | 41.1 |
| 21.256 | 4.17666 | 4124 | 27.4 |
| 22.209 | 3.99947 | 1596 | 10.6 |
| 23.056 | 3.8544 | 6004 | 39.9 |
| 24.7 | 3.60148 | 10306 | 68.4 |
| 26.751 | 3.3298 | 5273 | 35 |
| 27.087 | 3.28933 | 9892 | 65.7 |
| 28.575 | 3.12132 | 2804 | 18.6 |
| 29.431 | 3.03244 | 3483 | 23.1 |
| 29.822 | 2.9936 | 3436 | 22.8 |
| 30.098 | 2.96674 | 3503 | 23.3 |

Example 34

XRPD of (3S)-4-{4-[3-(3-methylpiperidin-1-yl)propoxy]phenyl}pyridine 1-oxide orotate

| Angle 2-Theta ° | d value Angstrom | Intensity Count | Intensity % |
|---|---|---|---|
| 6.813 | 12.96356 | 14761 | 39.6 |
| 9.3 | 9.50134 | 18344 | 49.2 |
| 10.122 | 8.73237 | 3418 | 9.2 |
| 11.855 | 7.45922 | 7872 | 21.1 |
| 12.343 | 7.16534 | 3390 | 9.1 |
| 12.501 | 7.07484 | 3560 | 9.5 |
| 13.478 | 6.56449 | 11038 | 29.6 |
| 13.917 | 6.35833 | 7063 | 18.9 |
| 14.698 | 6.02225 | 37281 | 100 |
| 15.431 | 5.73774 | 21914 | 58.8 |
| 15.989 | 5.53869 | 4110 | 11 |
| 16.864 | 5.25309 | 4780 | 12.8 |
| 17.276 | 5.12873 | 3309 | 8.9 |
| 17.681 | 5.01219 | 3628 | 9.7 |
| 18.559 | 4.777 | 5347 | 14.3 |
| 19.312 | 4.59236 | 3299 | 8.8 |
| 19.872 | 4.46431 | 14550 | 39 |
| 20.148 | 4.4037 | 24954 | 66.9 |
| 20.709 | 4.2857 | 12916 | 34.6 |
| 21.67 | 4.09771 | 7765 | 20.8 |
| 22.132 | 4.01324 | 2894 | 7.8 |
| 22.587 | 3.93339 | 6133 | 16.5 |
| 23.543 | 3.77583 | 6696 | 18 |
| 23.714 | 3.74903 | 17914 | 48.1 |
| 24.57 | 3.62024 | 4148 | 11.1 |
| 24.773 | 3.59103 | 4372 | 11.7 |
| 26.78 | 3.32627 | 9867 | 26.5 |
| 27.489 | 3.24215 | 5566 | 14.9 |

Example 35

XRPD of (3S)-4-{4-[3-(3-methylpiperidin-1-yl)propoxy]phenyl}pyridine 1-oxide 5-sulfosalicylate

| Angle 2-Theta ° | d value Angstrom | Intensity Count | Intensity % |
|---|---|---|---|
| 9.06 | 9.75257 | 62819 | 100 |
| 10.527 | 8.3971 | 16700 | 26.6 |
| 12.577 | 7.03267 | 5252 | 8.4 |
| 13.308 | 6.64783 | 1079 | 1.7 |
| 13.584 | 6.5132 | 926 | 1.5 |

-continued

| Angle 2-Theta ° | d value Angstrom | Intensity Count | Intensity % |
|---|---|---|---|
| 14.254 | 6.20861 | 1613 | 2.6 |
| 15.037 | 5.88707 | 1759 | 2.8 |
| 15.684 | 5.64577 | 2314 | 3.7 |
| 16.393 | 5.40291 | 1195 | 1.9 |
| 16.486 | 5.37284 | 1259 | 2 |
| 17.265 | 5.13193 | 3028 | 4.8 |
| 17.687 | 5.01041 | 15149 | 24.1 |
| 18.031 | 4.91572 | 17071 | 27.2 |
| 18.728 | 4.7344 | 2909 | 4.6 |
| 19.457 | 4.55849 | 900 | 1.4 |
| 19.734 | 4.49526 | 1532 | 2.4 |
| 20.329 | 4.36498 | 1242 | 2 |
| 21.038 | 4.21934 | 53363 | 84.9 |
| 21.4 | 4.14883 | 8088 | 12.9 |
| 22.087 | 4.0214 | 1663 | 2.6 |
| 22.497 | 3.94889 | 1674 | 2.7 |
| 25.608 | 3.47579 | 2201 | 3.5 |
| 26.327 | 3.38247 | 10817 | 17.2 |
| 26.943 | 3.30654 | 1451 | 2.3 |
| 28.177 | 3.16447 | 1393 | 2.2 |
| 28.314 | 3.14945 | 1695 | 2.7 |
| 28.958 | 3.08091 | 1642 | 2.6 |
| 30.641 | 2.91539 | 1824 | 2.9 |

Example 36

XRPD of (3S)-4-{4-[3-(3-methylpiperidin-1-yl)propoxy]phenyl}pyridine 1-oxide 1-hydroxy-2-naphtoate

| Angle 2-Theta ° | d value Angstrom | Intensity Count | Intensity % |
|---|---|---|---|
| 6.468 | 13.65521 | 3347 | 5.4 |
| 7.141 | 12.36906 | 40644 | 65.1 |
| 9.093 | 9.71746 | 4334 | 6.9 |
| 11.546 | 7.65819 | 1516 | 2.4 |
| 12.784 | 6.91889 | 62472 | 100 |
| 13.168 | 6.71807 | 46091 | 73.8 |
| 14.379 | 6.15501 | 4351 | 7 |
| 15.312 | 5.78209 | 1350 | 2.2 |
| 16.007 | 5.53236 | 3604 | 5.8 |
| 16.916 | 5.23712 | 1499 | 2.4 |
| 17.313 | 5.11804 | 4582 | 7.3 |
| 18.162 | 4.88047 | 4156 | 6.7 |
| 18.877 | 4.69727 | 4259 | 6.8 |
| 19.337 | 4.5866 | 2607 | 4.2 |
| 20.286 | 4.37401 | 35807 | 57.3 |
| 20.632 | 4.30154 | 4252 | 6.8 |
| 21.257 | 4.17639 | 4957 | 7.9 |
| 21.503 | 4.12927 | 30954 | 49.5 |
| 21.993 | 4.03835 | 10314 | 16.5 |
| 23.084 | 3.84988 | 5338 | 8.5 |
| 23.2 | 3.83085 | 4238 | 6.8 |
| 23.75 | 3.74343 | 3716 | 5.9 |
| 24.787 | 3.58902 | 1870 | 3 |
| 25.123 | 3.54186 | 1231 | 2 |
| 25.665 | 3.46825 | 31154 | 49.9 |
| 26.265 | 3.39038 | 9578 | 15.3 |
| 26.643 | 3.34311 | 1547 | 2.5 |
| 27.343 | 3.2591 | 3973 | 6.4 |
| 27.44 | 3.24775 | 5471 | 8.8 |
| 28.073 | 3.176 | 9106 | 14.6 |
| 28.802 | 3.09719 | 8293 | 13.3 |
| 29.31 | 3.04465 | 2719 | 4.4 |
| 31.423 | 2.84464 | 2681 | 4.3 |

Example 37

XRPD of (3S)-4-{4-[3-(3-methylpiperidin-1-yl)propoxy]phenyl}pyridine 1-oxide 3-hydroxy-2-naphtoate phase A

| Angle 2-Theta ° | d value Angstrom | Intensity Count | Intensity % |
|---|---|---|---|
| 7.446 | 11.86322 | 30252 | 49.7 |
| 8.748 | 10.10043 | 1368 | 2.2 |
| 9.024 | 9.7917 | 1609 | 2.6 |
| 9.937 | 8.8938 | 6257 | 10.3 |
| 11.27 | 7.84506 | 60862 | 100 |
| 13.293 | 6.6553 | 2270 | 3.7 |
| 15.072 | 5.87339 | 43369 | 71.3 |
| 19.59 | 4.52783 | 6152 | 10.1 |
| 19.98 | 4.44042 | 2834 | 4.7 |
| 24.813 | 3.5854 | 7358 | 12.1 |
| 25.124 | 3.54169 | 3602 | 5.9 |
| 26.85 | 3.31777 | 4592 | 7.5 |

Example 38

XRPD of (3S)-4-{4-[3-(3-methylpiperidin-1-yl)propoxy]phenyl}pyridine 1-oxide 3-hydroxy-2-naphtoate phase B

| Angle 2-Theta ° | d value Angstrom | Intensity Count | Intensity % |
|---|---|---|---|
| 6.311 | 13.99407 | 6977 | 9.6 |
| 7.159 | 12.3387 | 72823 | 100 |
| 8.95 | 9.87282 | 7257 | 10 |
| 11.342 | 7.79538 | 966 | 1.3 |
| 12.631 | 7.00249 | 2500 | 3.4 |
| 13.122 | 6.7414 | 13203 | 18.1 |
| 14.111 | 6.27121 | 1300 | 1.8 |
| 15.45 | 5.73069 | 1989 | 2.7 |
| 15.864 | 5.58187 | 25710 | 35.3 |
| 17.022 | 5.20487 | 3579 | 4.9 |
| 17.934 | 4.9421 | 8356 | 11.5 |
| 18.147 | 4.88456 | 1440 | 2 |
| 18.916 | 4.68768 | 5385 | 7.4 |
| 20.202 | 4.39198 | 15208 | 20.9 |
| 20.29 | 4.37317 | 14155 | 19.4 |
| 21.317 | 4.16482 | 40284 | 55.3 |
| 21.92 | 4.05165 | 4786 | 6.6 |
| 22.918 | 3.87737 | 1388 | 1.9 |
| 23.873 | 3.72441 | 2539 | 3.5 |
| 24.888 | 3.57474 | 4225 | 5.8 |
| 25.607 | 3.47602 | 846 | 1.2 |
| 26.162 | 3.40345 | 1922 | 2.6 |
| 27.012 | 3.29822 | 7527 | 10.3 |
| 27.403 | 3.25209 | 1911 | 2.6 |
| 27.913 | 3.19376 | 1445 | 2 |
| 28.62 | 3.11652 | 3777 | 5.2 |
| 31.941 | 2.79964 | 1710 | 2.3 |

Example 39

XRPD of (3S)-4-{4-[3-(3-methylpiperidin-1-yl)propoxy]phenyl}pyridine 1-oxide glycolate

| Angle 2-Theta ° | d value Angstrom | Intensity Count | Intensity % |
|---|---|---|---|
| 7.495 | 11.78525 | 29684 | 51 |
| 11.196 | 7.89645 | 22907 | 39.3 |

| Angle 2-Theta ° | d value Angstrom | Intensity Count | Intensity % |
|---|---|---|---|
| 14.884 | 5.94733 | 58231 | 100 |
| 15.032 | 5.88902 | 37813 | 64.9 |
| 18.675 | 4.74765 | 13995 | 24 |
| 18.833 | 4.70819 | 10947 | 18.8 |
| 22.371 | 3.97094 | 3746 | 6.4 |
| 23.744 | 3.74433 | 2259 | 3.9 |
| 24.252 | 3.66704 | 1859 | 3.2 |

The invention claimed is:

1. A method for the treatment of disorders selected from Alzheimer's disease; attention; wakefulness and memorization disorders; cognitive deficits in psychiatric pathologies; cognitive, mood and vigilance disorders; depressive or asthenic states; Parkinson's disease; obstructive sleep apnea; dementia with Lewy bodies; vascular dementia; vertigo; motion sickness; obesity; diabetes and the metabolic syndrome; sleep disorders; stress; psychotropic disorders; epilepsy; depression; narcolepsy with or without cataplexy; disorders of the hypothalamohypophyseal secretion, the cerebral circulation and/or immune system; excessive daytime sleepiness and/or for facilitating night works or adaptation to time shift in healthy humans; substance abuse disorders; substance abuse withdrawal syndromes; attention deficit disorders; post-stroke fatigue, mood, cognitive and vigilance disorders; cognitive disorders in autism; chronic pain and chronic fatigue; attention and vigilance disorders of ADHD (attention-deficit hyperactivity disorder) in children or adults or following cerebrovascular accidents, said method comprising administering (3S)-4-{4-[3-(3-methylpiperidin-1-yl)propoxy]phenyl}pyridine 1-oxide of formula (A):

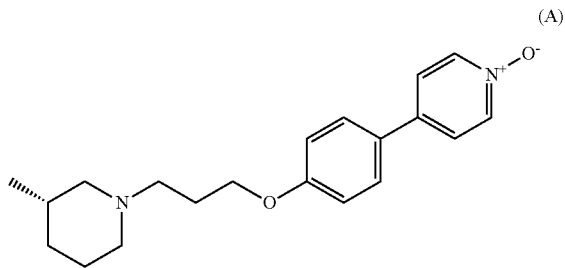 [SMILES: C[C@H]1CCCN(CCCOc2ccc(-c3cc[n+]([O-])cc3)cc2)C1]

or its pharmaceutically acceptable salts and/or the solvates of said compound (A) or of its salts, in a human patient at a dose of base comprised between 10 and 90 µg a day relative to compound (A) in the form of the base.

2. The method according to claim 1, wherein the sleep disorders are selected from the group consisting of insomnia, disorders of sleep initiation and maintenance, sleep fragmentation, parasomnias, REM sleep disorders, sleep disordered breathing, circadian dysrhythmia, narcolepsy with or without cataplexy, and excessive daytime sleepiness.

3. The method according to claim 1, wherein compound (A) is in the form of its pharmaceutically acceptable salts selected from the group consisting of hydrochloride, oxalate, dihydrochloride, hydrobromide, dihydrobromide, naphthalene-1,5-disulfonate, sulfate, ethane-1,2-disulfonate, cyclamate, toluenesulfonate, paratoluenesulfonate, thiocyanate, nitrate, methanesulfonate, dodecylsulfate, naphthalene-2-sulfonate, benzenesulfonate, dichloroacetate, glycerophosphate, 2-hydroxyethanesulfonate, aspartate, maleate, phosphate, ethanesulfonate, camphor-10-sulfonate, glutamate, alginate, pamoate, 2-oxo-glutarate, 1-hydroxy-2-naphthoate, malonate, gentisate, salicylate, tartrate, fumarate, galactarate, citrate, glucuronate, lactobionate, 4-aminosalicylate, glycolate, sesquiglycolate, glucoheptonate, pyroglutamate, mandelate, malate, hippurate, formate, gluconate, lactate, oleate, ascorbate, benzoate, succinate, 4-acetamidobenzoate, glutarate, cinnamate, adipate, sebacate, camphorate, acetate, caproate, nicotinate, isobutyrate, proionate, carate, laurate, palmitate, stearate, undecen-10-oate, caprylate, orotate, carbonate, 5-sulfocalicylate, 1-hydroxy-2-naphtoate, 3-hydroxy-2-naphtoate; and/or solvates.

4. The method according to claim 1, wherein compound (A) is in the form of a hydrochloride.

5. The method according to claim 1, wherein compound (A) is in the form of a dihydrochloride salt.

6. The method according to claim 1, wherein compound (A) is in the form of a tetrahydrate of dihydrochloride.

7. The method according to claim 1, wherein the daily dose for administration to a human patient is comprised between 20 and 50 µg a day relative to compound (A) in the form of the base.

8. The method according to claim 1, wherein the daily dose for administration to a human is comprised between 30 to 45 µg a day relative to compound (A) in the form of the base.

9. The method according to claim 1, wherein compound (A) is administered once a day or once every two days.

10. The method according to claim 1, wherein compound (A) is administered once a day.

11. The method according to claim 1, wherein compound (A) is administered via the oral route.

12. The method according to claim 1, wherein compound (A) is chosen from the group consisting of:
(3S)-4-{4-[3-(3-methylpiperidin-1-yl)propoxy] phenyl}pyridine 1-oxide dihydrochloride tetrahydrate;
(3S)-4-{4-[3-(3-methylpiperidin-1-yl)propoxy] phenyl}pyridine 1-oxide oxalate;
(3S)-4-{4-[3-(3-methylpiperidin-1-yl)propoxy] phenyl}pyridine 1-oxide L-tartrate and its trihydrate;
(3S)-4-{4-[3-(3-methylpiperidin-1-yl)propoxy] phenyl}pyridine 1-oxide pamoate;
(3S)-4-{4-[3-(3-methylpiperidin-1-yl)propoxy] phenyl}pyridine 1-oxide fumarate;
(3S)-4-{4-[3-(3-methylpiperidin-1-yl)propoxy] phenyl}pyridine 1-oxide para-toluenesulfonate and its sestertihydrate (2.5)
(3S)-4-{4-[3-(3-methylpiperidin-1-yl)propoxy] phenyl}pyridine 1-oxide 1,5-naphtalenedisulfonate, and its hemiethanolate monohydrate;
(3S)-4-{4-[3-(3-methylpiperidin-1-yl)propoxy] phenyl}pyridine 1-oxide phosphate;
(3S)-4-{4-[3-(3-methylpiperidin-1-yl)propoxy] phenyl}pyridine 1-oxide bromhydrate;
(3S)-4-{4-[3-(3-methylpiperidin-1-yl)propoxy] phenyl}pyridine 1-oxide 1,2-ethanedisulfonate;
(3S)-4-{4-[3-(3-methylpiperidin-1-yl)propoxy] phenyl}pyridine 1-oxide sulfate;
(3S)-4-{4-[3-(3-methylpiperidin-1-yl)propoxy] phenyl}pyridine 1-oxide dibromhydrate;
(3S)-4-{4-[3-(3-methylpiperidin-1-yl)propoxy] phenyl}pyridine 1-oxide orotate and its dihydrate;
(3S)-4-{4-[3-(3-methylpiperidin-1-yl)propoxy] phenyl}pyridine 1-oxide 5-sulfosalicylate;

(3S)-4-{4-[3-(3-methylpiperidin-1-yl)propoxy]phenyl}pyridine 1-oxide 1-hydroxy-2-naphtoate and its monohydrate;

(3S)-4-{4-[3-(3-methylpiperidin-1-yl)propoxy]phenyl}pyridine 1-oxide 3-hydroxy-2-naphtoate; and (3S)-4-{4-[3-(3-methylpiperidin-1-yl)propoxyl]phenyl}pyridine 1-oxide (sesqui)glycolate and its monohydrate.

13. A compound chosen from the group consisting of:

(3S)-4-{4-[3-(3-methylpiperidin-1-yl)propoxy]phenyl}pyridine 1-oxide dihydrochloride tetrahydrate;

(3S)-4-{4-[3-(3-methylpiperidin-1-yl)propoxy]phenyl}pyridine 1-oxide L-tartrate and its trihydrate;

(3S)-4-{4-[3-(3-methylpiperidin-1-yl)propoxy]phenyl}pyridine 1-oxide pamoate;

(3S)-4-{4-[3-(3-methylpiperidin-1-yl)propoxy]phenyl}pyridine 1-oxide fumarate;

(3S)-4-{4-[3-(3-methylpiperidin-1-yl)propoxy]phenyl}pyridine 1-oxide para-toluenesulfonate and its sestertihydrate (2.5)

(3S)-4-{4-[3-(3-methylpiperidin-1-yl)propoxy]phenyl}pyridine 1-oxide 1,5-naphtalenedisulfonate, and its hemiethanolate monohydrate;

(3S)-4-{4-[3-(3-methylpiperidin-1-yl)propoxy]phenyl}pyridine 1-oxide phosphate;

(3S)-4-{4-[3-(3-methylpiperidin-1-yl)propoxy]phenyl}pyridine 1-oxide bromhydrate;

(3S)-4-{4-[3-(3-methylpiperidin-1-yl)propoxy]phenyl}pyridine 1-oxide 1,2-ethanedisulfonate;

(3S)-4-{4-[3-(3-methylpiperidin-1-yl)propoxy]phenyl}pyridine 1-oxide sulfate;

(3S)-4-{4-[3-(3-methylpiperidin-1-yl)propoxy]phenyl}pyridine 1-oxide dibromhydrate;

(3S)-4-{4-[3-(3-methylpiperidin-1-yl)propoxy]phenyl}pyridine 1-oxide orotate and its dihydrate;

(3S)-4-{4-[3-(3-methylpiperidin-1-yl)propoxy]phenyl}pyridine 1-oxide 5-sulfosalicylate;

(3S)-4-{4-[3-(3-methylpiperidin-1-yl)propoxy]phenyl}pyridine 1-oxide 1-hydroxy-2-naphtoate and its monohydrate;

(3S)-4-{4-[3-(3-methylpiperidin-1-yl)propoxy]phenyl}pyridine 1-oxide 3-hydroxy-2-naphtoate; and (3S)-4-{4-[3-(3-methylpiperidin-1-yl)propoxy]phenyl}pyridine 1-oxide (sesqui)glycolate and its monohydrate.

14. The method according to claim 1, wherein the excessive daytime sleepiness is selected from the group consisting of excessive daytime sleepiness and fatigue associated with Parkinson's disease, with obstructive sleep apnea or with dementia.

15. The method according to claim 2, wherein the excessive daytime sleepiness is selected from the group consisting of sleep attacks and excessive daytime sleepiness associated with Parkinson's disease, with obstructive sleep apnea or with dementia.

16. The method according to claim 1, wherein the substance abuse disorder is alcohol abuse disorder.

17. The method according to claim 3, wherein the solvates are selected from the group consisting of hydrates, ethanolate, and hemiethanolate.

18. The method of claim 1, wherein the cognitive, mood and vigilance disorders are cognitive, mood and vigilance disorders in aged persons.

* * * * *